US012784909B2

(12) United States Patent
Almuhaideb et al.

(10) Patent No.: US 12,784,909 B2
(45) Date of Patent: *Nov. 3, 2026

(54) SMART GATE WITH TEMPERATURE RESPONSIVE CONTROL

(71) Applicant: Imam Abdulrahman Bin Faisal University, Dammam (SA)

(72) Inventors: Abdullah Mohammed Almuhaideb, Dammam (SA); Mariam Ahmed Mustafa Elhussein, Dammam (SA); Fatema Jaffer Alholyal, Dammam (SA); Zainab Mohamed Kadour, Dammam (SA); Leena Saleh Alghamdi, Dammam (SA); Maram Abdullah Alawami, Dammam (SA); Majd Taleb Al-Ismail, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 19 days.

This patent is subject to a terminal disclaimer.

(21) Appl. No.: 19/189,830

(22) Filed: Apr. 25, 2025

(65) Prior Publication Data

US 2025/0253042 A1 Aug. 7, 2025

Related U.S. Application Data

(63) Continuation of application No. 17/895,202, filed on Aug. 25, 2022, now Pat. No. 12,380,999.

(51) Int. Cl.
*G16H 40/63* (2018.01)
*G06K 7/14* (2006.01)

(52) U.S. Cl.
CPC .......... *G16H 40/63* (2018.01); *G06K 7/1417* (2013.01)

(58) Field of Classification Search
None
See application file for complete search history.

(56) References Cited

U.S. PATENT DOCUMENTS 12,380,999 B2 * 8/2025 Almuhaideb ........ G06K 7/1417
2015/0105687 A1 * 4/2015 Abreu .................... A61B 5/002
600/549

(Continued)

FOREIGN PATENT DOCUMENTS

WO 2011/005224 A1 1/2011

OTHER PUBLICATIONS

COVID-19 eGate Screening System ; Sydney IoT Platform, The University of Sydney ; 16 pages.

(Continued)

*Primary Examiner* — Chad A Newton
(74) *Attorney, Agent, or Firm* — Oblon, McClelland, Maier & Neustadt, L.L.P.

(57) ABSTRACT

A smart gate system, and method, includes a thermal sensor for measuring a temperature of a visitor and transmitting the measured temperature, a QR code reader to read a health status QR code having a date range and transmitting a message including health status information of the visitor and a request for entry, a gate controller receiving a control signal for permitting or denying entry through a gate, a server for determining that the health status information and the temperature of the visitor indicate that the visitor has not contracted a predetermined virus and that the visitor is a registered visitor, and responding to the request for entry by transmitting the control signal to the gate controller in accordance with the determination and whether the health status QR code is within the predetermined date range, and the gate controller controlling opening of the gate based on the control signal.

9 Claims, 23 Drawing Sheets

(56) References Cited

U.S. PATENT DOCUMENTS

| | | | | |
|---|---|---|---|---|
| 2021/0010867 | A1* | 1/2021 | Li | G01J 5/021 |
| 2021/0012869 | A1 | 1/2021 | Kotlarz | |
| 2021/0304537 | A1* | 9/2021 | Reed | G06F 18/22 |
| 2021/0335072 | A1 | 10/2021 | Caldwell et al. | |
| 2021/0358244 | A1 | 11/2021 | Chafni | |
| 2022/0111091 | A1* | 4/2022 | Hatamian | A61L 2/18 |
| 2022/0223300 | A1 | 7/2022 | Ferro, Jr | |

OTHER PUBLICATIONS

Biometric Contactless Attendance & Temperature System ; Adera ; 15 Pages.

* cited by examiner

Related Art

Related Art

200

Related Art

Related Art

Related Art

900

SMART GATE WITH TEMPERATURE RESPONSIVE CONTROL

CROSS-REFERENCE TO RELATED APPLICATIONS

The present application is a Continuation of U.S. application Ser. No. 17/895,202, now allowed, having a filing date of Aug. 25, 2022.

STATEMENT OF ACKNOWLEDGEMENT

The authors would like to acknowledge the support provided by Imam Abdulrahman Faisal University (IAU), Dammam, Saudi Arabia, for this work.

BACKGROUND

Field of the Invention

The present disclosure relates generally to a smart portal system that can determine an individual's health identity including whether the individual(s) have received a particular vaccination, and determine whether the individual(s) are authorized to enter a restricted area, and in particular a portal system that can read the QR code of a Tawakkalna application to determine an individuals' vaccination status and measure current body temperature as prerequisite for authorization for entry.

Description of the Related Art

In order to enter any facility in the Kingdom of Saudi Arabia, it is required that a person establish that precautions against diseases such as the Covid-19 virus have been taken, for example by taking two doses of the vaccine, and that the vaccination be verified by a health identity through the "Tawakkalna" (aka Tawakulna) application, which appears in green on the screen of a mobile device, by appearance of the word immunized and/or a corresponding symbol or message. See Tawakkalna available at: ta.sdaia.gov.sa/index Sep. 20, 2021, incorporated herein by reference in its entirety.

A security person such as a health inspector or policeman can easily verify the health identity of an individual, but the process requires a long wait time, especially if the facility is big, such as in the case of a large university. It is advantageous that the health identity of each employee and student can be verified without delaying the start of work. Unfortunately, this would require the presence of many security persons. One solution is to use smart gates.

COVID-19 is a type of dangerous virus, and many people throughout the world have lived through difficult conditions during the spread of this virus and its variants. Unfortunately, the manual verification of health identity (e.g., vaccination status) requires the security person to be close to the individuals, which exposes the security person to the risk of contracting diseases, especially since the security person checks to ensure that a mask is worn and measures the body temperature.

However, a significant problem facing a high percentage of people who commute to work each day is traffic congestion that may be created or exacerbated by health checks at the entry points to different facilities, such as university campuses, supermarkets, hospitals, colleges, etc. This is due to the lengthy process of manual verification of health status. For instance, a campus gate may have a long line of traffic due to the manual health status check that takes a lot of time. As a consequence, due to the traffic congestion, staff and students will be late for work and classes.

Several approaches have been proposed to address the problems associated with verifying health identity of large groups of people. In 2020 a new method for smart doors that uses Bluetooth to control the door's lock was introduced. This method is composed of three main elements. The first element is the overall design based on Bluetooth control that consists of many components such as the central controller, door lock controller, Bluetooth communication module, and system keyboard. The second element is the hardware design of the smart door lock. The third element is the software design, and it consists of the control software of the smart door and the Bluetooth software for the mobile client device. This method is efficient and flexible, and has shown to be economical. See Z. Mu, W. Li, C. Lou and M. Liu, "Investigation and Application of Smart Door Locks based on Bluetooth Control Technology," 2020 Asia-Pacific Conference on Image Processing, Electronics and Computers (IPEC), 2020, pp. 68-72, doi: 10.1109/IPEC49694.2020.9115189.

Also in 2020, an access control schema using WIFI bridges for a smart lock was presented. See Andrew Zhang and Raghavendra V. P. P. ICRAI 2020:2020 6th International Conference on Robotics and Artificial Intelligence November 2020 Pages 174-178https://doi.org/10.1145/3449301.3449331. This plan depends on WIFI bridges and a cloud server. It also uses A ES256 symmetric encryption, Bluetooth energy, and HTTPS communications to introduce an enhanced system that does not require physical monitoring or a human being's presence. The smart door has proven its successfulness as it provides 24/7 control and monitoring of the lock.

Still further in 2020, in order to overcome the weakness of a face recognition access control system, Bintang Wahyudono and Dion Ogi studied the possibility of implementing two authentication factors in one system. See B. Wahyudono and D. Ogi, "Implementation of Two Factor Authentication based on RFID and Face Recognition using LBP Algorithm on Access Control System," 2020 International Conference on ICT for Smart Society (ICISS), 2020, pp. 1-6, doi: 10.1109/ICISS50791.2020.9307564. FIG. 1 illustrates an RFID gate for controlling entry. Whyudono et al. implemented the system with two authentication factors of RFID 102 and face recognition based on a camera 104 using a local binary pattern algorithm. The access control system showed a major success using RFID with 100% authentication and 80% with face recognition with an average time of 0.03 seconds for RFID authentication and 6.3885 seconds for face recognition verification.

Also in 2020, Y aoqiu Hong designed an intelligent access control system using a DES-encrypted two-dimensional code. See Y. Hong, "Design of Intelligent Access Control System Based on DES Encrypted QR Code," 2020 IEEE International Conference on Advances in Electrical Engineering and Computer Applications (AEECA), 2020, pp. 1005-1008, doi: 10.1109/AEECA49918.2020.9213475. System components consist of an embedded access control system, Android smartphone terminal, and server management terminal. When the embedded access control system receives the user's instruction after authentication, it controls an electric door switch after passing verification. Applications installed on the Android smartphone are responsible for generating and sending QR codes for authentication. The server controls the multi-doors and users and manages the permissions of all users. Specifically, the system workflow includes opening the access control app on the smartphone, generating encrypted QR code images, setting the phone against the embedded access control system, identifying QR codes via the camera, and allowing the door to open after authentication. The authenticated users can send one QR code image to the non-authenticated users via mobile phone, giving them one chance to open the door. To prevent the QR code from being copied, the QR code has an expiration date. When the time limit is exceeded, the QR code cannot be used to open the door. The server side is responsible for recording and storing people's access information and status. Using the server, the administrator can change a user's authority, control multiple doors, and achieve centralized management.

Moving to the year 2021 and using IoT technologies, scientists Stuti Mehra and others designed a special control system for hospitals, especially for the infant room, based on human face recognition technology and remote monitoring. See S. Mehra, A. Khatri, P. Tanwar and V. Khatri, "Intelligent Embedded Security control system for Maternity ward based on IoT and Face recognition," 2018 International Conference on Advances in Computing, Communication Control and Networking (ICACCCN), 2018, pp. 49-53, doi: 10.1109/ICA CCCN.2018.8748516. The system regulates the entry of a person according to identity and gender, which helps provide security. The system works by using a face detection and recognition algorithm and ZigBee to find the person's identity. Then, another wireless interface is used to update the database in case there is a new person. If there is a new person, another alert message is sent. The system consists of a camera and a smart lock. The camera recognizes the person. The Face Recognition first sees whether the person is male/female. If the face is male, then the visitor waits for the visitation hours that are available for visiting the patient. If the sensor detects that the person is female and pregnant, then the system allows them to enter. If the person is a doctor, then the system checks the database for information about the doctor. The system checks IDs that are taken using the RFID technique and compares the IDs with their database. If the information in the IDs matches information in the database correctly, then the gate opens, otherwise not.

One approach to automatic access control has been to implement access control using a circuit board. In 2020, Jianfeng Y el proposed a method to set the lighting level, which is composed of a relay to control the ambient lighting level of the camera and a stepper motor to control the lighting of the curtain. See J. Ye, "Design and Implementation of Entrance Guard System Based on Face Recognition," 2020 International Conference on Virtual Reality and Intelligent Systems (ICVRIS), 2020, pp. 419-422, doi: 10.1109/ICVRIS51417.2020.00105. FIG. 2 illustrates a circuit diagram of a fingerprint biometric access control. The circuit 200 uses feedback from pre-processing of the picture and lighting level settings to control the adaptive lighting level of the objects in the captured image. The method is convenient and straightforward in design, exceptionally reliable, and easy to install. In conjunction with a PC, a camera records images and performs facial recognition, supported by ultrasonic distance measurement and infrared recognition of the human body. With the access control circuit 200 equipped with an infrared counter 202, the single-chip computer communicates with the PC through the USB serial port 204 to complete the coordinated operation of the access control and facial recognition system.

In addition, in 2021 scientists Terene Govender and Patrice U menne studied the possibility of implementing a secure smart gate system using fingerprint biometrics in conjunction with an Arduino Uno that is used to provide access to a home security gate. See T. Govender and P. Umenne, "Design of a Fingerprint Biometric Access Control System with GSM Functionality," 2021 International Conference on Artificial Intelligence, Big Data, Computing and Data Communication Systems (icA BCD), 2021, pp. 1-6, doi: 10.1109/icABCD51485.2021.9519320. The system contained the following: PC/IDE software, fingerprint modules, LED lights, servomotor, GSM module, LCD display, push buttons. If an unauthorized person tries to enter, the Arduino Uno microcontroller will send a text message to the security person or the owner of the house telling him that someone is trying to break in. When an authorized fingerprint is scanned, the system grants entry correctly. The test result was correct 71% of the time. If an unauthorized fingerprint is scanned, the system rejects access 100% of the time. Finally, when there is unauthorized access, the system sends an SM S correctly to the occupant's cellphone via the GSM module 89% of the time.

In 2021, scientists Dickey Dwi Putra et al. provided a solution in the form of Integrated COVID-19 Early Prevention Devices (INCEPS) which was proposed to prevent the spread of COVID-19 in a public area through an AI-based smart portal and website integration. See D. D. Putra, M. Febriyanto, M. M. Nadra, W. Shalannanda, E. R. Firzal and A. Munir, "Design of Smart-Gate Based on Artificial Intelligence Possibly for COVID-19 Early Prevention at Public Area," 2020 14th International Conference on Telecommunication Systems, Services, and Applications (TSSA, 2020, pp. 1-4, doi: 10.1109/TSSA51342.2020.9310878. INCEPS can monitor community density in various places and can provide a reminder to the public for further adherence to health protocols recommended by the government. FIG. 3 illustrates a smart-gate based on Artificial Intelligence for COVID-19 early prevention at a public area. The system consists of several components: an automatic gate 302, a temperature sensor 304, a tuned camera 306 for facial recognition, a disinfectant spraying box 308, and a disinfectant gate 310. When a person enters, their temperature is measured using the temperature sensor 304, then the camera 306 determines whether the person is wearing a mask or not, and based on the result, the gate 302 is opened. Otherwise, an alarm will ring. The data is recorded in the (INCEPS) database and displayed at the site to determine the number of visitors at an entrance before going to it.

In most cases, smart gates verify the identity of visitors or verify the validity of their access. The verification process is generally not done correctly except when using a variety of different authentication techniques. Several types of authentication have been previously addressed in research. The search for authentication was customized using QR and barcode because the "Tawakkalna" application displays the health status through them. Facial recognition was used in the verification of the presence of masks.

The general definition of biometric technologies is the measure of a human being's pattern. Biometrics consists of two types. The first one is behavioral biometric, which uses the pattern of individual actions such as a signature. The other type is physiological biometrics, and it focuses on the pattern of something in the human body, like the fingerprint. In this invention, the focus is on physiological biometrics.

The world situation and obligations imposed by the Covid-19 virus on the world, including the requirement to wear masks on faces and social distance, have led to various approaches to implement these requirements. Baluprithviraj K N and others proposed, in research they conducted in 2021, an authentication system that recognizes faces and will not give access to anyone who does not wear a mask. See K. N. Baluprithviraj, K. R. Bharathi, S. Chendhuran and P. Lokeshwaran, "Artificial Intelligence based Smart Door with Face Mask Detection," 2021 International Conference on Artificial Intelligence and Smart Systems (ICAIS), 2021, pp. 543-548, doi: 10.1109/ICAIS50930.2021.9395807. FIG. 4 illustrates access control turnstiles with facial recognition biometrics. An AI-based smart device (e.g., Raspberry pi with AI model and camera) and system 402 is linked to an application on the phone 404 that can be controlled through the application. Also, scientists Akshay Duth and others have created a hardware portal that can detect signs of COVID-19 disease. See A. Duth, A. A. Nambiar, C. B. Teja and S. Yadav, "Smart Door System with COVID-19 Risk Factor Evaluation, Contactless Data Acquisition and Sanitization," 2021 International Conference on Artificial Intelligence and Smart Systems (ICAIS), 2021, pp. 1504-1511, doi: 10.1109/ICAIS50930.2021.9395875. Based on symptoms and results, the hardware portal can give access to an individual by using an OpenCV system. The hardware portal starts by checking for the presence of a mask using a Raspberry Pi module and a camera module. Then, the hardware portal checks the temperature. The customer needs not have to touch any of the surfaces, even for opening the door. The entire system is completely automatic and is completely contactless.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

There remains a need to automate the process of entering various facilities and speed up the process. In conjunction, there is a need to limit the number of people in the facility, as well as to determine a number of people that would be allowed to enter.

SUMMARY

An aspect of the present disclosure is a smart gate system that can include a thermal sensor for measuring a temperature of a visitor and transmitting the measured temperature; a QR code reader to read a health status QR code and transmitting a message including health status information of the visitor in accordance with the health status QR code and a request for entry, the health status QR code having a predetermined date range; a database system for receiving and maintaining the health status information and registered visitor information; a gate controller receiving a control signal for permitting or denying entry through a gate; a server for determining that the health status information and the temperature of the visitor obtained from the thermal sensor indicate that the visitor has not contracted a predetermined virus and that the visitor is a registered visitor, and responding to the request for entry by transmitting the control signal to the gate controller in accordance with the determination and whether the health status QR code is within the predetermined date range; and the gate controller controlling opening of the gate based on the control signal that permits entry through the gate.

A further aspect is a smart gate system for vehicles that can include at least one terminal having a thermometer and a QR code reader; a server for receiving a reading from the thermometer, and health status information and date range from the QR code reader, and determining authorization to enter through a gate based on the thermometer reading, the health status information, and the date range, and sending an confirmation signal indicating authorization to enter, or denying entry; a microcontroller for opening a gate based on the confirmation signal and based on an operation signal from a security terminal to allow a single vehicle to pass through the opened gate; and a timer to time a predetermined duration that the gate remains open.

A further aspect is a smart gate system that can include a smart bracelet device having a memory storing health information of a user wearing the smart bracelet device and a communication circuit; a mobile device having a communication circuit for communication with the smart bracelet device, and a display device for graphical and textual display; a QR code reader reading a health status QR code from the display device of the mobile device; a server for receiving a body temperature reading from the smart bracelet device, and health status information and date range from the QR code reader, and determining authorization to enter through a gate based on the body temperature reading, the health status information, and the date range, and sending an authorization signal indicating authorization to enter, or denying entry; a microcontroller for opening a gate based on the authorization signal to allow the user wearing the smart bracelet device to pass through the opened gate; and a timer to time a predetermined duration that the gate remains open.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features.

The characteristics and advantages of exemplary embodiments are set out in more detail in the following description, made with reference to the accompanying drawings. In the drawings.

DETAILED DESCRIPTION

Figure 1:
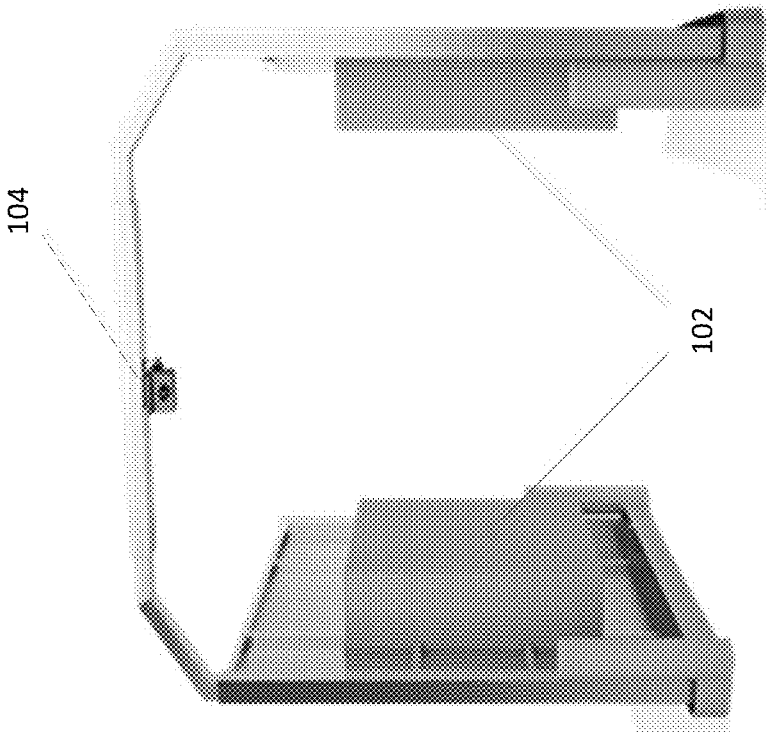
FIG. 1 illustrates an RFID gate for controlling entry.
Figure 2:
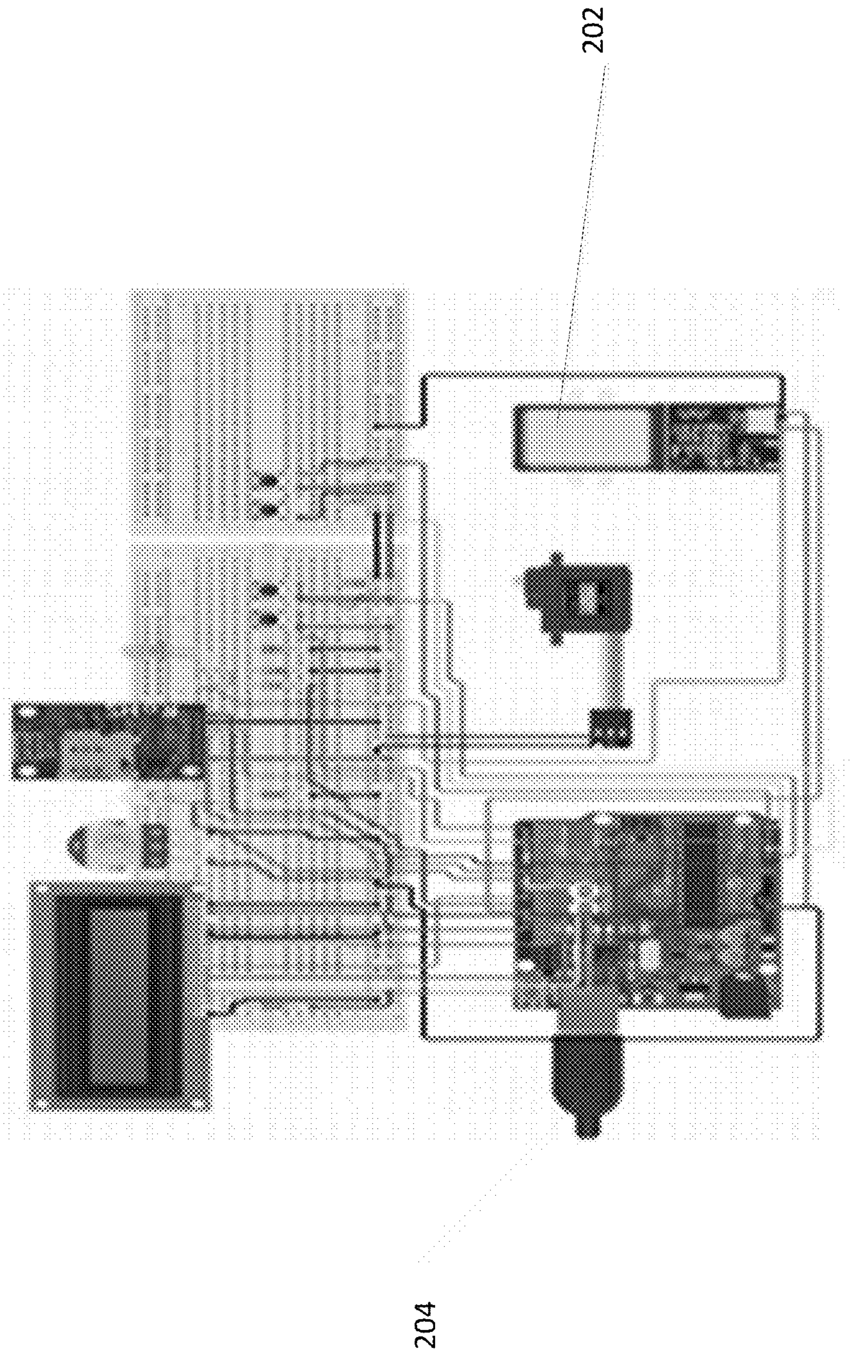
FIG. 2 illustrates a circuit diagram of a fingerprint biometric access control device.
Figure 3:
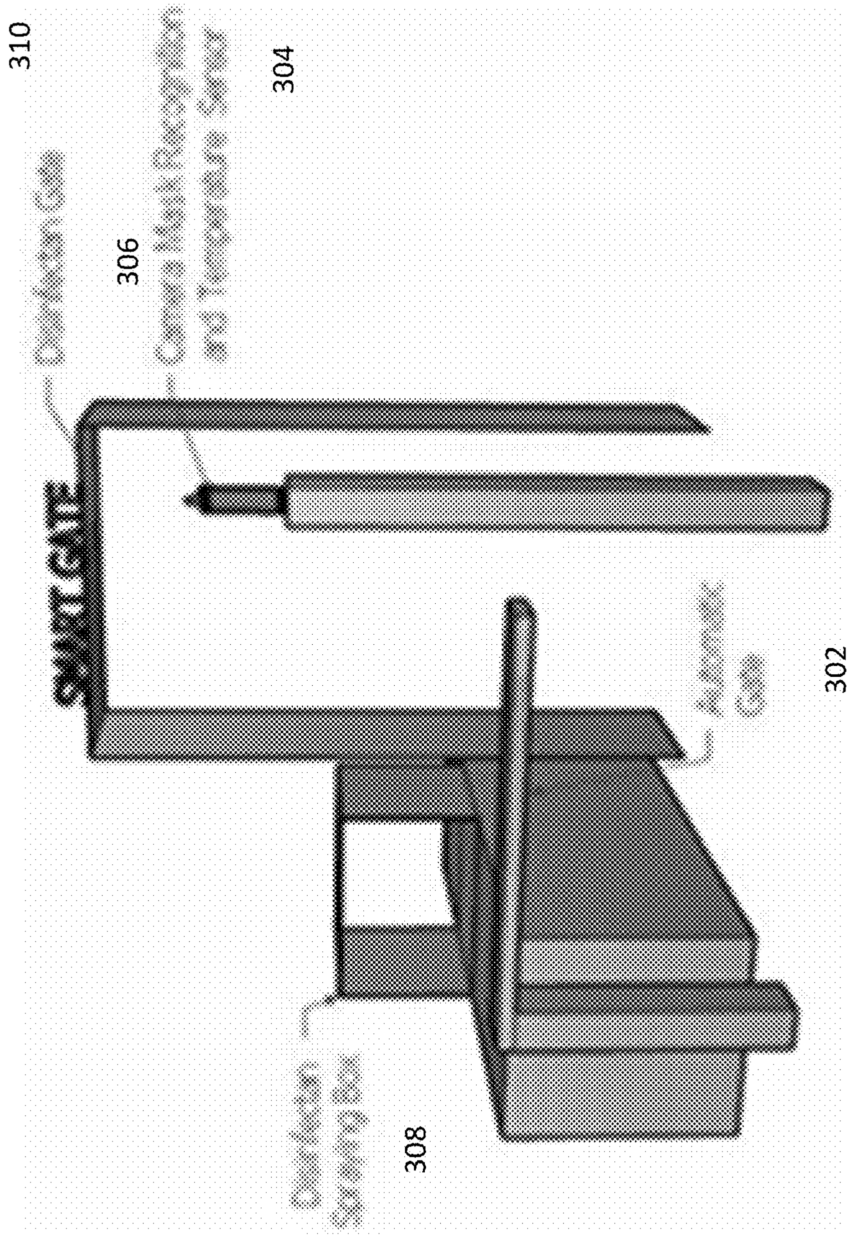
FIG. 3 illustrates a smart gate for COVID-19 early prevention at a public area.
Figure 4:
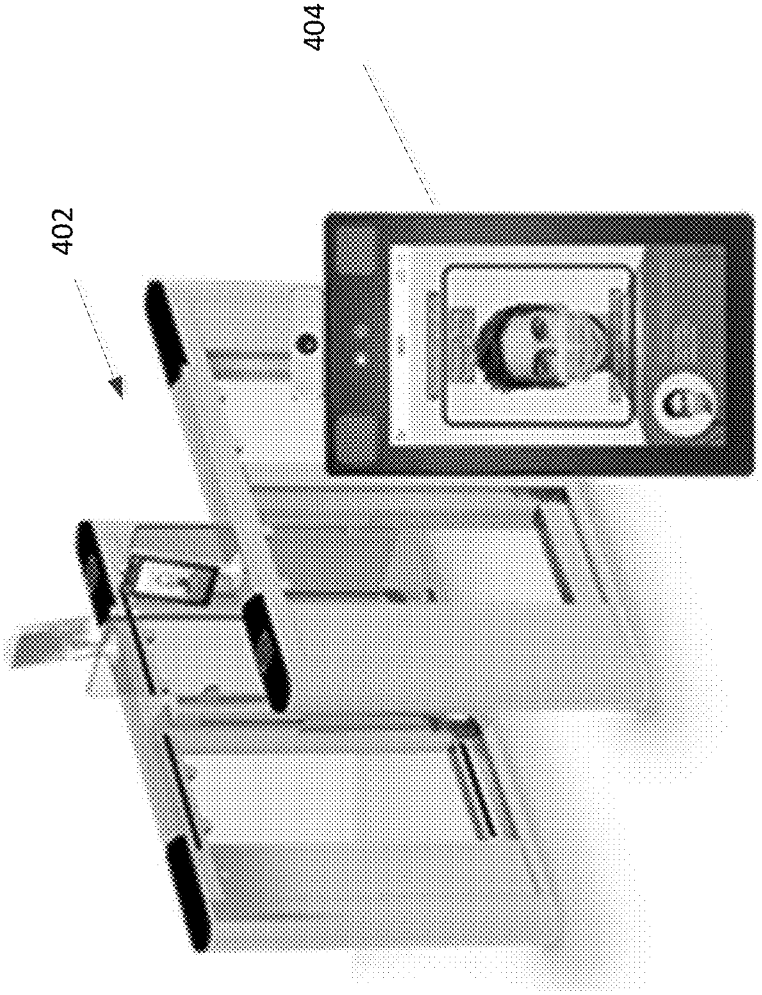
FIG. 4 illustrates access control turnstiles with facial recognition biometrics.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) may be practiced without those specific details. In some instances, well-known structures and components may be shown in block diagram form in order to avoid obscuring the concepts of the disclosed subject matter.

As used herein any reference to "one embodiment" or "some embodiments" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. In addition, the articles "a" and "an" as used in this application and the appended claims are to be construed to mean "one or more" or "at least one" unless specified otherwise.

Furthermore, the terms "approximately," "proximate," "minor," and similar terms generally refer to ranges that include the identified value within a margin of 20%, 10% or preferably 5% in certain embodiments, and any values therebetween.

Referring now to the drawings, wherein like reference numerals designate identical or corresponding parts throughout several views, the following description relates to a system and method for a smart portal system that can determine an individual's health state and whether they have got a particular vaccination, and then determine whether they are authorized to enter or not using a QR code and health state.

In most government, public and private institutions, there are two types of people who can enter: employees and visitors. What distinguishes the employees from the visitors is that the employees can access personal data registered in the employer's database, while the visitors typically have no personal data saved and/or do not have access to personal data. Under pandemic restrictions when a visitor enters an institution, the visitor is now to check body temperature, in addition to verifying the status of Covid-19 vaccination, in addition the individual submits to inspection by thermal camera to identify whether the individual is wearing a mask and/or is suffering a fever. Further, upon checking whether the person's temperature is in the normal range or not, an access gate can open and allow the person to enter or prevent entry. A problem with this approach is that a large percentage of security (e.g., a large human labor force and hardware footprint) is necessary to prevent unauthorized persons from entering the establishment.

Figure 5:
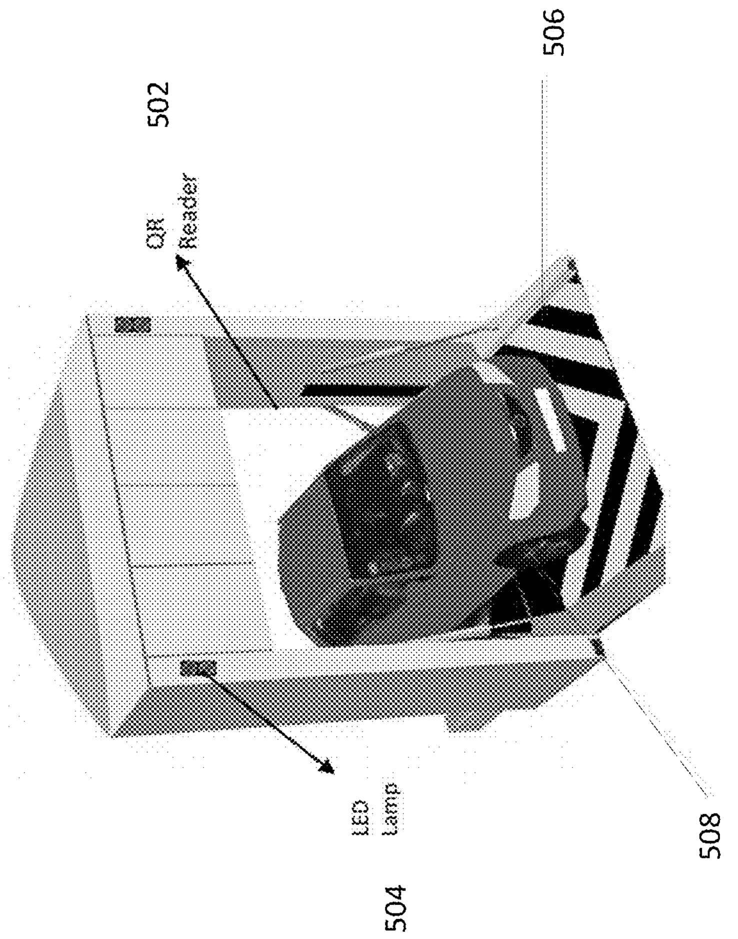
FIG. 5 illustrates a QR code reader apparatus.

The concept of a Unique QR code Identification (UQID) system has several potential uses, including improving hospitality solutions in hotels, access control in parking areas, and the development of more intelligent home automation technology. In the case of hotels, the correct QR code is used to unlock or keep the door locked accordingly. In the case of a hotel, the hotel can send the guest a QR code when they register for a room. That QR code is used as the key they need to access the room. FIG. 5 illustrates one example identification system that uses QR code for entry into a parking area. A QR reader 502 can scan the QR code for a vehicle 508, or a person in the vehicle. A gate 506 may drop when an indicator lamp (LED lamp 504) indicates that the QR code allows entry. In the case of home security solutions, QR code authentication promises to be one of the most accessible, user-friendly, and cost-effective. QR code authentication can replace conventional keys such as swipe cards or tokens and make authentication more practical. In addition to being cheaper than biometric systems, the UQID system enables good software security as well.

Offices have also increasingly been utilizing smart doors in the last decade. Due to the popularity of smartphones, there is a rising demand from consumers for the ability to do everything they need in their day-to-day lives through their mobile devices. Security is automated with the system, requiring little maintenance and monitoring. The UQID system provides security hardware and software solutions at lower costs and a more minimalistic design that is more welcoming to users and guests alike.

Figure 6:
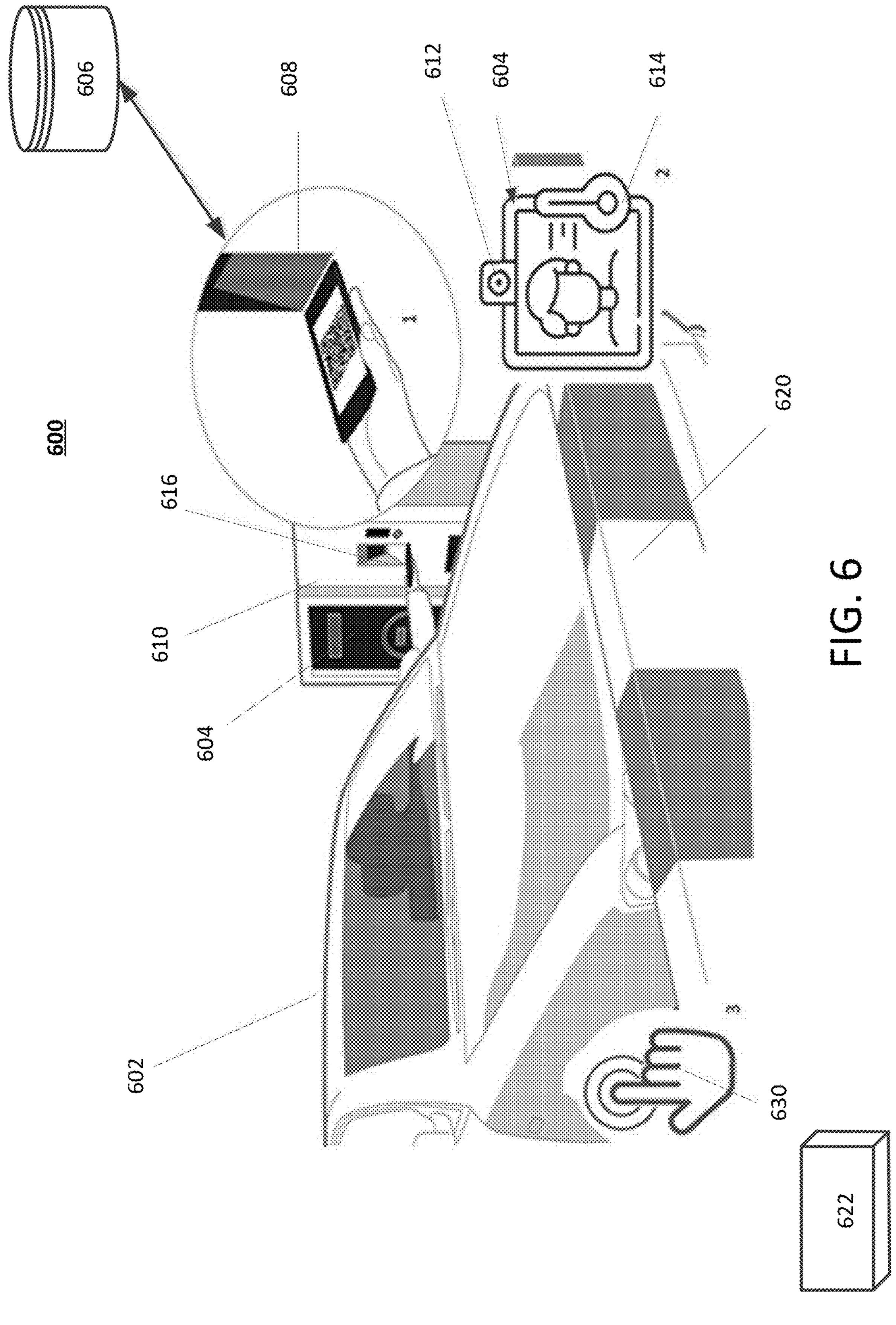
FIG. 6 illustrates a smart gate system configured with hardware interfaces in accordance with exemplary aspects of the disclosure.

FIG. 6 illustrates a smart gate system configured with hardware interfaces in accordance with exemplary aspects of the present disclosure. In one embodiment, the smart gate system 600 is configured for verifying the identity and health status of a person in a vehicle 602. The smart gate system 600 can detect whether there is more than one person in the vehicle 602, in which case, the smart gate system 600 will require verification of health identity of all persons in the vehicle 602. In an embodiment, the smart gate system 600 includes an infrared camera to detect the number of persons in a vehicle. In one embodiment, the smart gate system 600 is configured to verify health identity of persons in the vehicle from both sides of the vehicle 602.

The smart gate system 600 includes a terminal 610, having a display device 604 and a QR code reader 616, as a connected tool. In one embodiment, there may be multiple terminals to accommodate multiple persons in a vehicle 602. Data is transferred from the terminal 610 to a personal device 608 in the form of a QR code and the QR code reader 616 retrieves the health status of the user by using the QR code as a unique identifier. The personal device 608 is connected to an external database server 606. The connection to the external database server 606 is managed by the operating system of the personal device 608, which may be a mobile phone or other portable display device. The terminal 610 includes a temperature sensor 610 to verify that the temperature of a person in the vehicle 602 does not exceed a threshold, e.g., greater than 38 degrees Celsius. The smart gate system 600 can include an emergency button 630. In the case of the occurrence of an emergency or other problem, a person in the vehicle 602 can press the emergency button 630 to call and request a security person.

The smart gate system 600 includes a gate operation mechanism 622. The gate operation mechanism 622 includes a motor unit for opening and closing a gate 620, a controller for controlling the motor, a motion sensor, such as an infrared sensor or laser, for determining whether a vehicle is passing the gate 620 boundary, and a timer mechanism. In operation, the gate operating mechanism 622 may close the gate 620 based on the timer mechanism. In an embodiment, the closing process depends on timing by the timer mechanism that times out after a preset time such as 3 seconds, followed by a sensor that checks the passage of the vehicle 602 pass the opened gate 620. If the vehicle 602 does not pass the opened gate within the 3 seconds, the timer restarts. The gate 620 is closed three seconds after the vehicle 602 has passed the gate 620. A purpose of the timing mechanism is to control flow of vehicles through the smart gate so as smooth the flow of individuals entering the facility, as well as to prevent another vehicle(s) from passing through the smart gate without being verified. The time out setting of the timing mechanism may be adjustable and may be set at a different time out period.

In an embodiment, the gate 620 is a door that raises and lowers. The gate operating mechanism 622 may raise and lower the door.

It is advantageous to make sure that the smart gate system 600 remains secure. The smart gate system 600 is preferably configured such that nobody who is unworthy can enter the gate. In an embodiment, security is achieved when a certified security guard is present to ensure the gate is not opened by persons who do not meet the requirements (such as those without two doses of vaccination and an unstable temperature). Subsequently, if there is no authorized security person, or if the security guard's shift time has expired, the gate will be left in manual mode, and the gate will not be responsible for letting people in.

The smart gate system 600 includes a communication architecture arranged as a client-server model. In an example embodiment, the client is the smart gate terminal 610 which communicates with a back end server. In addition, a database server 606 can be accessed by the personal device 608 for obtaining information about the user's health status. The terminal 610 may include an access control system that reads the health status information of the user obtained from the database server 606. Also, the health status information may be displayed in a display device of the terminal 610 as a web page using a web browser. In addition, communication between the personal device 608 and the smart gate terminal 610 needed to meet requirements for doing communication functions in the smart gate system 600 can include wireless communications such as Wi-Fi and Bluetooth.

Figure 7:
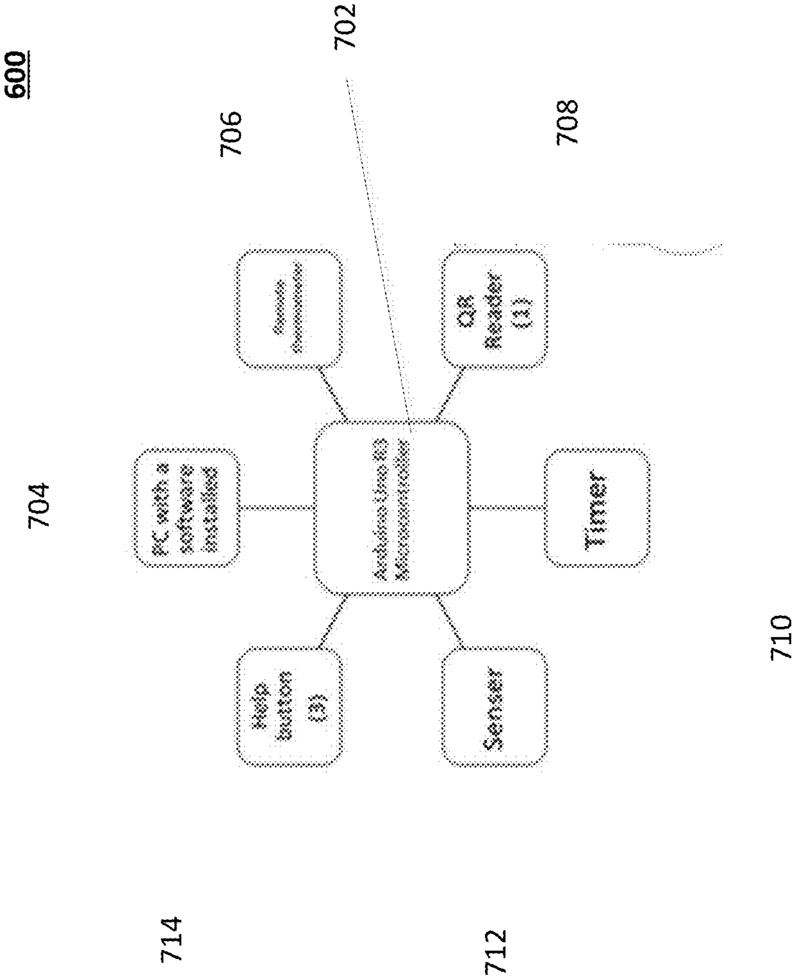
FIG. 7 is a block diagram for a smart gate system in accordance with exemplary aspects of the disclosure.

FIG. 7 is a diagram of a relationship between components of a smart gate system in an exemplary hardware design.

(Microcontroller 702) A microcontroller 702 is used to control the operation of the peripheral components connected to it to perform access control for the Smart Gate System as shown in FIG. 6. In an exemplary embodiment, the microcontroller 702 of the Smart Gate System is an Arduino Uno or the like. The Arduino Uno is an open-source platform used for hardware programming. The Arduino Uno can be programmed to perform a particular function. In the exemplary embodiment, the Arduino Uno receives its commands from Smart Gate System software.

The microcontroller 702 may work in conjunction with a computer system 704 with software for performing functions of the smart gate system, such as for transmitting health identification.

(Remote thermometer 706) An important health factor is normal body temperature, and exceeding the normal body temperature may be an indicator of infection with various diseases or some pandemic viruses (such as the Covid 19 virus), so there is a temperature sensor device that measures the body temperature and checks that it is in the normal range for a human. In an exemplary embodiment, the temperature sensor device 706 can send the data to the Arduino Uno Microcontroller 702.

(QR reader 708) A QR code is a machine-readable optical label that contains information. A QR code is a square made up of small square patterns. The placement of these small squares encrypts the information in the QR code. After scanning, a QR code provides information. A QR Code Scanner/Reader 708 is an optical reader that can read QR codes. It is used in the smart gate system to read the QR code and verify the health status provided in the Tawakkalna application.

(Power key) In some embodiments, a power key may be provided to transfer the gate mode from an automatic mode to a manual mode.

(Timer 710) A timing device 710 measures time and can issue a signal to a machine in order to start and stop operations at a specific time. The timing device 710 is used on the smart gate system to measure the time the gate will remain open for a car to pass the gate. See E. Wong, "Schneiderman's Eight Golden Rules will help you design better interfaces," Interaction-design.org. Available: www.interactiondesign.org/literature/article/shneiderman-s-eight-golden-rules-will-help-you-design-better-interfaces. [Accessed: 21 Nov. 2021]

(Help Button 714) A help button 714 can function to provide assistance to users as quickly as possible to improve the efficiency of the smart gate system performance and responsiveness. When this help button 714 is pressed, an alert will be sent to the smart gate system to notify the security guards that there is an emergency case that needs help.

(Sensor 712) Utilizing a sensor 712 embedded with the gate is used to control the opening operation. After a visitor satisfies all the conditions and allows the visitor to enter, the gate will open, and the timer will work. The sensor 712 will sense if there is an existing object, such as a vehicle or person, and let it pass. The timer will start upon detecting that the vehicle or person has passed. When the timer times out, the smart gate system will close the gate.

To facilitate control of entry into an establishment, the smart gate system can be used for individual persons and vehicles, meaning that the equipment can be a gate that accommodates large vehicles or just large enough to accommodate an individual person. The smart gate system may perform a check count (defined as: (current vehicle weight-original unladen vehicle weight)/normal human weight).

It is essential to make sure that the smart gate system always remains secure. It must be ensured that nobody who lacks permission or is unworthy is able to enter the gate. Enhanced security is achieved by a certified security guard that is present to ensure that the gate is not opened by persons who do not meet the requirements for entry (such as those without two doses of vaccination and an unstable temperature). In cases where there is no authorized security person, or if the security guard's shift time has expired, the gate will be left in manual mode, and the gate will not control access for people coming in.

The smart gate system provides easy operation, reliability, safety, and security. Security guards and administrative staff can rely on these easy-to-use features to ensure that the gate works the way they expect it to.

Figure 8:
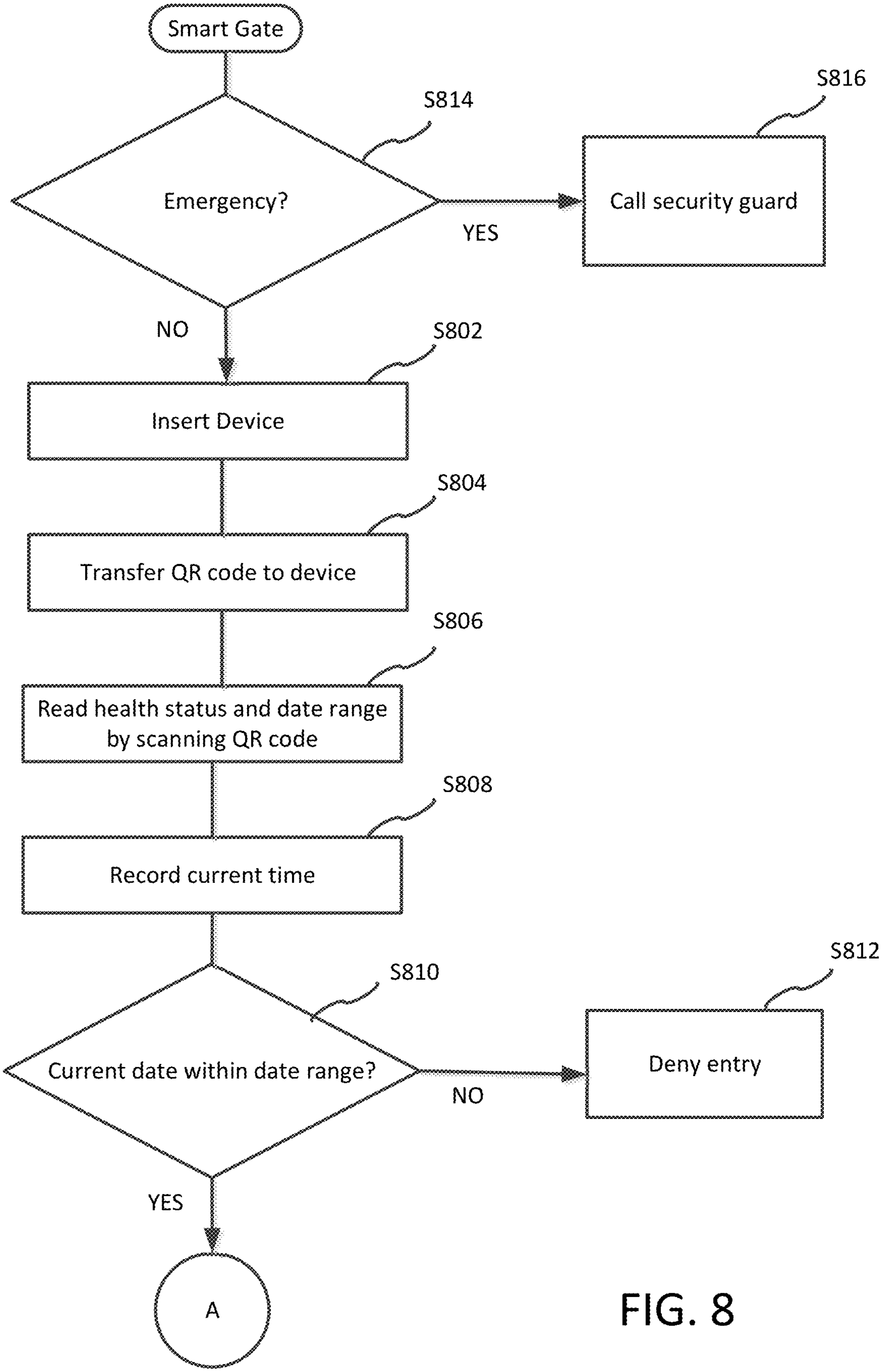
FIG. 8 is a flowchart for the operation of the smart gate system of FIG. 6.
Figure 8:
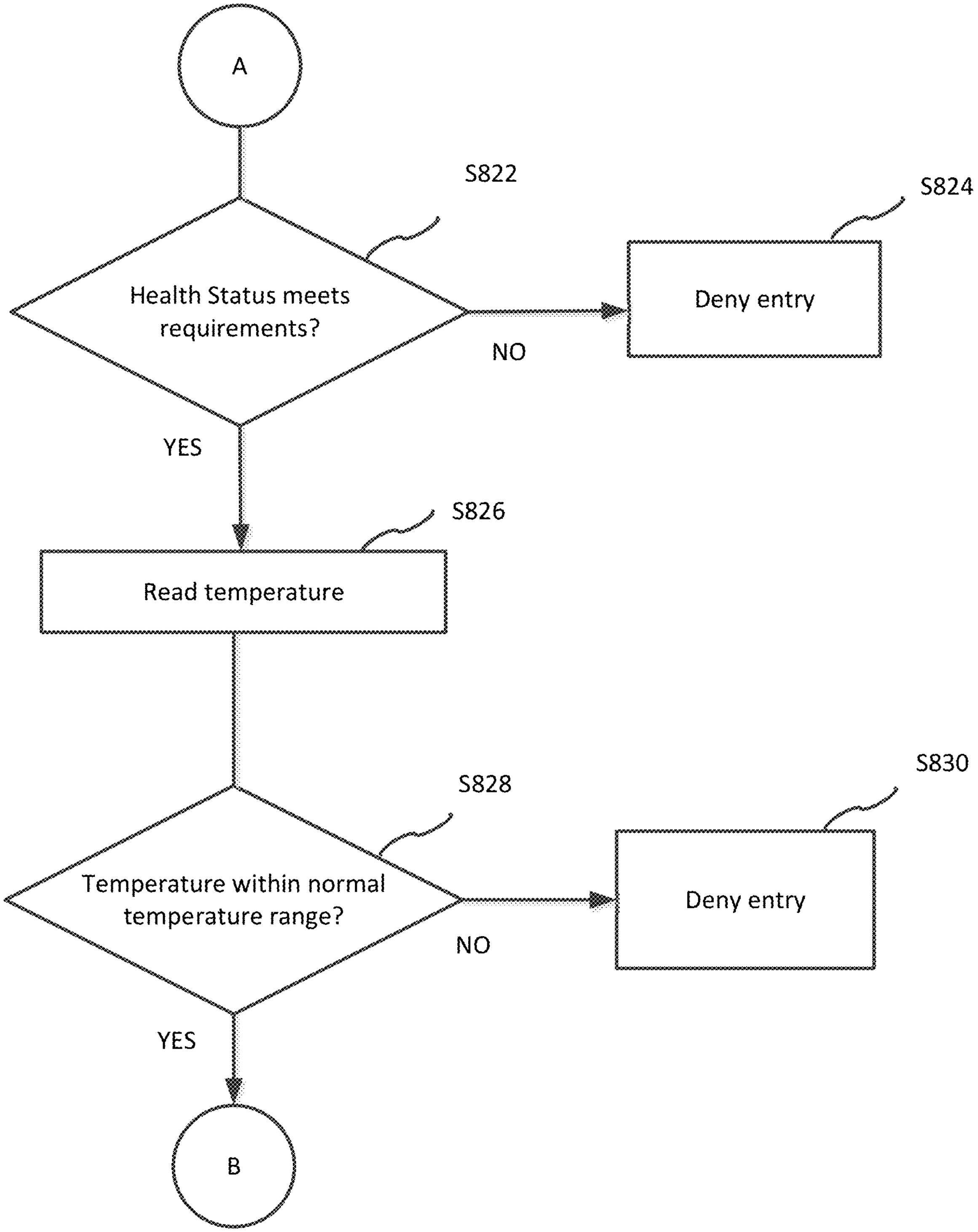
Figure 8:
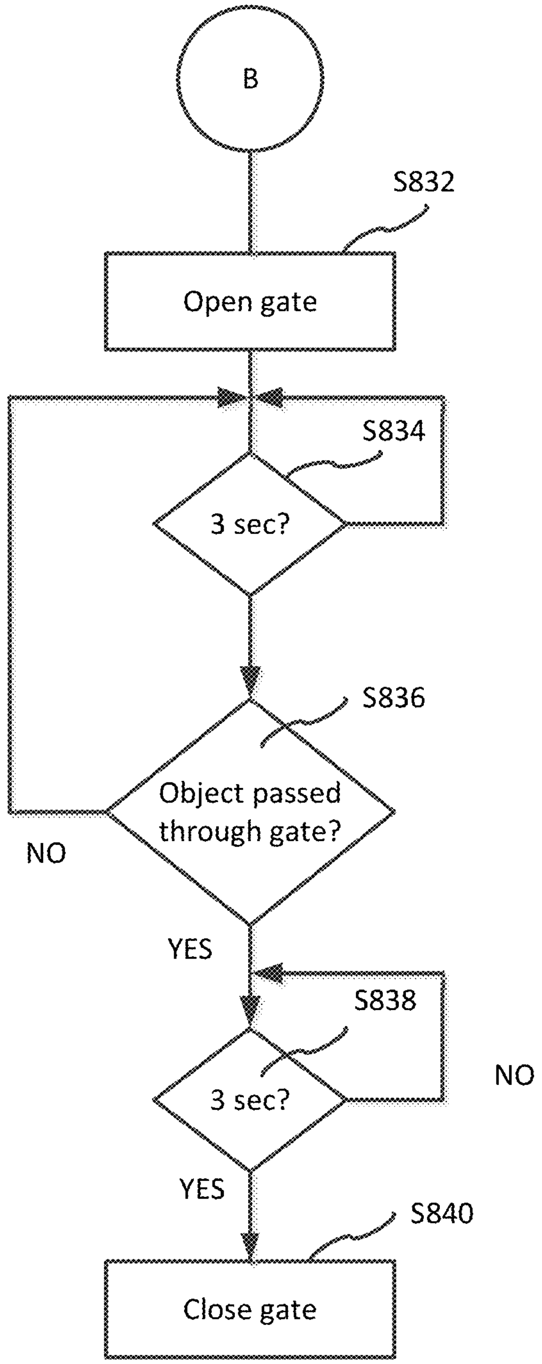

FIG. 8 is a flowchart for the operation of the smart gate system of FIG. 6. It should be understood that although the steps of the flowchart are shown in a certain sequence, some steps may be performed in parallel or in a different order. For example, the step S806 of reading the health status QR code from a display of a personal display device may be done in parallel with S816 reading body temperature by the thermal sensor. In another example, the step S816 of reading body temperature may be performed as an initial step, such that a health status QR code is not transmitted to the personal display device.

In an embodiment, the smart gate system 600 uses a QR code reader 616 as a connected tool. The QR code reader 606 may scan/read a QR code by inserting (S802) a personal device 608 into a slot in the QR code reader 616 or placing the personal device 608 in a position for reading by the QR code reader 616. In an embodiment, the QR code is an encrypted code to ensure that health status information is securely obtained and decoded by the reader. It should be noted that there may be situations where a user does not have a personal device 608, or their personal device 608 is inoperable. This situation could occur when the user has misplaced their personal device 608, does not own a personal device 608, or the battery of the personal device 608 requires recharging. In such a situation, the user may obtain a printed QR code before arriving at the smart gate system 600. In some embodiments, the security person or other official may assist the user in obtaining a printed QR code. The QR code reader 616 may be equipped to read a printed QR code.

In S804, the data will be transferred between the smart gate system 600 and the personal device 608 when the QR code is read to obtain the health status of the user. The connection of personal devices 608 to an external database server 606 is managed by the basic operating system on the personal device 608, e.g., mobile phone. In S806, the health status of the user and a date range of the QR code is obtained when the QR code is read.

In S808, the QR code reader 616 obtains the time and date that the QR code reader scans/reads the QR code. In S810, the smart gate system 600 determines whether the current date is within the date range of the QR code. If it is determined that the current date is after the date range (NO in S810), In S812, the smart gate system will send a message indicating that entry through the gate is denied.

In a case that the current date is within the date range of the QR code (YES in S810), in S822, the smart gate system 600 will determine if the health status meets requirements for entry. If the health status does not meet the requirements for entry (NO in S822), in S824, the smart gate system will send a message indicating that entry through the gate is denied.

In S826, the body temperature sensor 614 (706) senses body temperature and, in S828, the smart gate system 600 verifies whether the temperature is at or below 38 degrees Celsius. If the detected body temperature is above 38 degrees Celsius, in S830, the smart gate system 600 denies entry of the user.

In an embodiment, in S814, in the case that an emergency or other problem, in S816, the user can press the emergency button 630 (714) to request a security person.

As for the gate closing mechanism 622, the closing process depends on a timer mechanism 710 that measures time for a period of time, and a sensor 712 that checks the passage of an object pass the opened gate. In S822, provided that the user meets both health status and temperature requirements of S828 and there is no emergency condition in S814, in S832, the gate will be opened for three seconds, in S834. In S836, the sensor 712 will detect whether the object has passed through the opened gate. If not, the timer mechanism will restart. Otherwise, in S838, the timer mechanism 710 starts over and, in S840, closes the gate after three seconds.

Figure 9A:
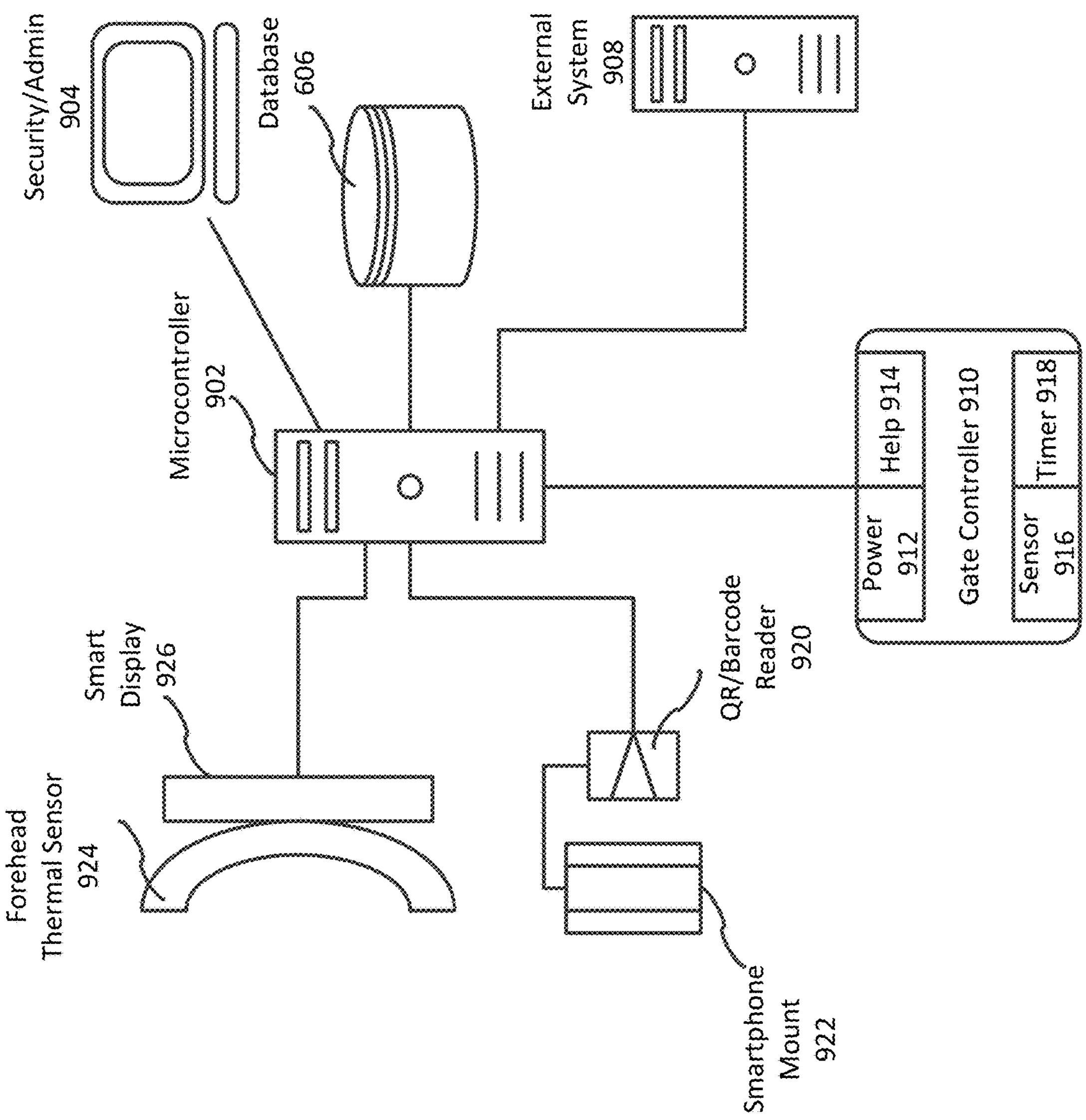
FIG. 9A is a schematic diagram of an exemplary smart gate system in accordance with exemplary aspects of the disclosure.

FIG. 9A is a schematic diagram of an exemplary smart gate system in accordance with exemplary aspects of the disclosure. An example hardware implementation of the smart gate system 900 may include an arrangement that accommodates a touch free approach to simultaneously obtain a person's temperature while reading a QR code. The arrangement may include a mount 922 for placing a smartphone and a motorized adjustable stand having a temperature sensor 924 for obtaining temperature of a person's forehead. The QR code is read by the QR code reader 920 when the smartphone is placed in the mount 922. The mobile device holder (mount 922) provides positioning of the mobile device to read QR code. The position of the mobile device automatically adjusts to the reader, or the QR reader adjusts to the QR code displayed on the mobile device. The motorized adjustable stand automatically adjusts to the height of the person's forehead to read the body temperature. A smart display 926 may display a pass or fail message to the user. In an embodiment, the smart display 926 may output a sound, to indicate that the forehead thermal sensor 924 is in the correct position to take a measurement, as well as to indicate pass or fail. Different sounds may be output for height adjustment and for pass or fail. A central microcontroller 902 may connect to the motorized adjustable stand, and in particular the thermal sensor 924 mounted on the stand, may connect to the QR reader 920, a gate controller 910, as well as a security or administrator terminal 904, a database server 606, and an external computer system 908. The gate controller 910 may include a power source 912, a help button 914, an object detection sensor 916 and a timer 918. The microcontroller 902 operates as an access control unit, while the gate controller 910 operates a gate.

In a preferable embodiment of the invention the forehead temperature sensor 924 is equipped with a spooled sheath screen protector to avoid contamination between use. For example, an individual using a forehead temperature sensor for measuring body temperature must makes physical contact with the forehead temperature sensor. This increases the risk that the individual may contaminate the sensor surface with a disease vector such as a bacterium or virus. Conventional forehead sensors are disinfected between uses. However, when embodied in the smart gate system of the present disclosure, disinfection by cleaning or disinfecting the contact surface with a disinfectant such as alcohol after each use is not practical.

Figure 9C:
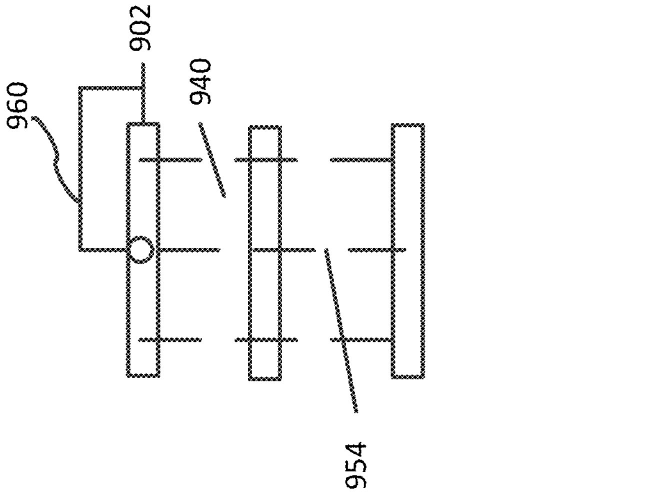
FIG. 9C shows a front view of the embodiment shown in FIG. 9B showing a protective sheath material covering a front surface of a forehead temperature sensor.
Figure 9B:
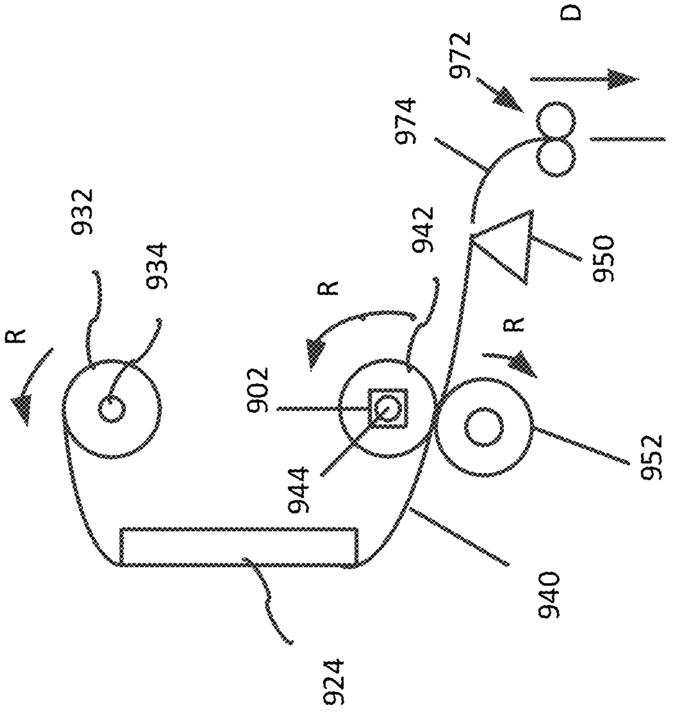
FIG. 9B shows an embodiment of the invention in which a forehead temperature sensor is covered with a spooled protective sheet.

Individual protective sheaths can be used for protecting temperature probes such as thermometers between uses. Each sheath is disposed after contact with an individual. This individual sheath strategy is not practical for inclusion in the smart gate system of the present disclosure because it requires a manual operator or a complex system for tearing away and replacing a contact sheath between uses. In FIG. 9B a spooled sheath screen protector provides a means to cover the forehead temperature sensor 924 with a protective surface between uses without interruption or manual disinfection of the system. A spooled sheath screen protector preferably includes a supply spool 932 (9-101) mounted above and behind the plane of the forehead temperature sensor 924. The supply spool 932 holds a rolled supply of protective sheath material 940 (9-110) for covering the contact surface of the forehead temperature sensor 924. The supply spool 932 rotates in direction R. A take up spool 942 (9-102) is mounted below the temperature sensor and behind the plane of the contact surface of the forehead temperature sensor 924. The take up spool 942 (9-102) functions to collect and re-spool protective sheath material 940 (9-110) that has contacted an individual during use. The take up spool 942 rotates in a direction R.

In one embodiment, the take up spool 942 may have an accompanying tension spool 952 to aid in pulling the protective sheath material 940 in a direction away from the forehead temperature sensor 924. Downstream of the take up spool 942 may include a cutting edge 950 that aligns with the perforation between sheets of protective sheath material 940 to aid in separation of a sheet. A pair of pinching rollers 972 may be used to pull and separate a sheet 974 so that the sheet 974 may be disposed of in a direction D.

The supply spool 932 is adapted to hold a spool of disposable protective sheath material 940 (9-110). The protective sheath material 940 (9-110) is provided on the supply spool 932 (9-101) in the form of long rolled individual perforated sheets and is advanced onto the take up spool 942 after each use of the forehead temperature sensor 924. The supply spool 932 (9-101) is equipped with a resistive despool decelerator 934 (9-111) such as a friction wheel to hinder uncontrolled or excessive release of the sheath. The take up spool 942 (9-102) is configured with a stepper motor 944 (9-112) that functions to rotate the take up spool thereby pulling a preset length of the protective sheath material from the supply spool after each use. The stepper motor is controlled by the microcontroller 902 to advance a preset length of protective sheath material 940 (9-110) such that the protective sheath material is retrieved onto the take up spool after completion of a forehead thermal sensor measurement. FIG. 9C shows a front view of the spooled sheath screen protector system. The protective sheath material 940 (9-110) is preferably configured with a conductive path 954 (9-116) traveling longitudinally through its length, e.g., a length of conductive polymer or metallic thread. A capacitive sensor 960 (9-115) mounted on one or both of the supply spool 932 (9-101) or the take up spool 942 (9-102) makes electrical contact with the conductive path 954 (9-116) to measure and record a capacitance value. The capacitance value reflects contact between and individual and the protective sheath material during a measurement occurrence on the forehead thermal sensor 924. The microcontroller 902 includes program instructions to advance the take up spool after a cycle of capacitative measurements which identify first contact of an edge of individual with the protective sheath material and separation of the individual from the protective sheath material and the forehead temperature sensor after a measurement event.

The micontroller 902 keeps a count of quantity of the protective sheath material and outputs a signal indicating a low level of the material below a predetermined level. The supply spool 932 and the take up spool 942 may each be replaced. The replacement may be performed manually, or using an automatic role feeder mechanism. In one embodiment, a shaft may be provided that can store additional supply spools 932, where a replacement spool 932 is dropped into place as the mounted spool is dropped out.

In one embodiment, the gate is a door and the gate controller 910 controls a motor operated lock to lock or unlock the door.

Figure 10:
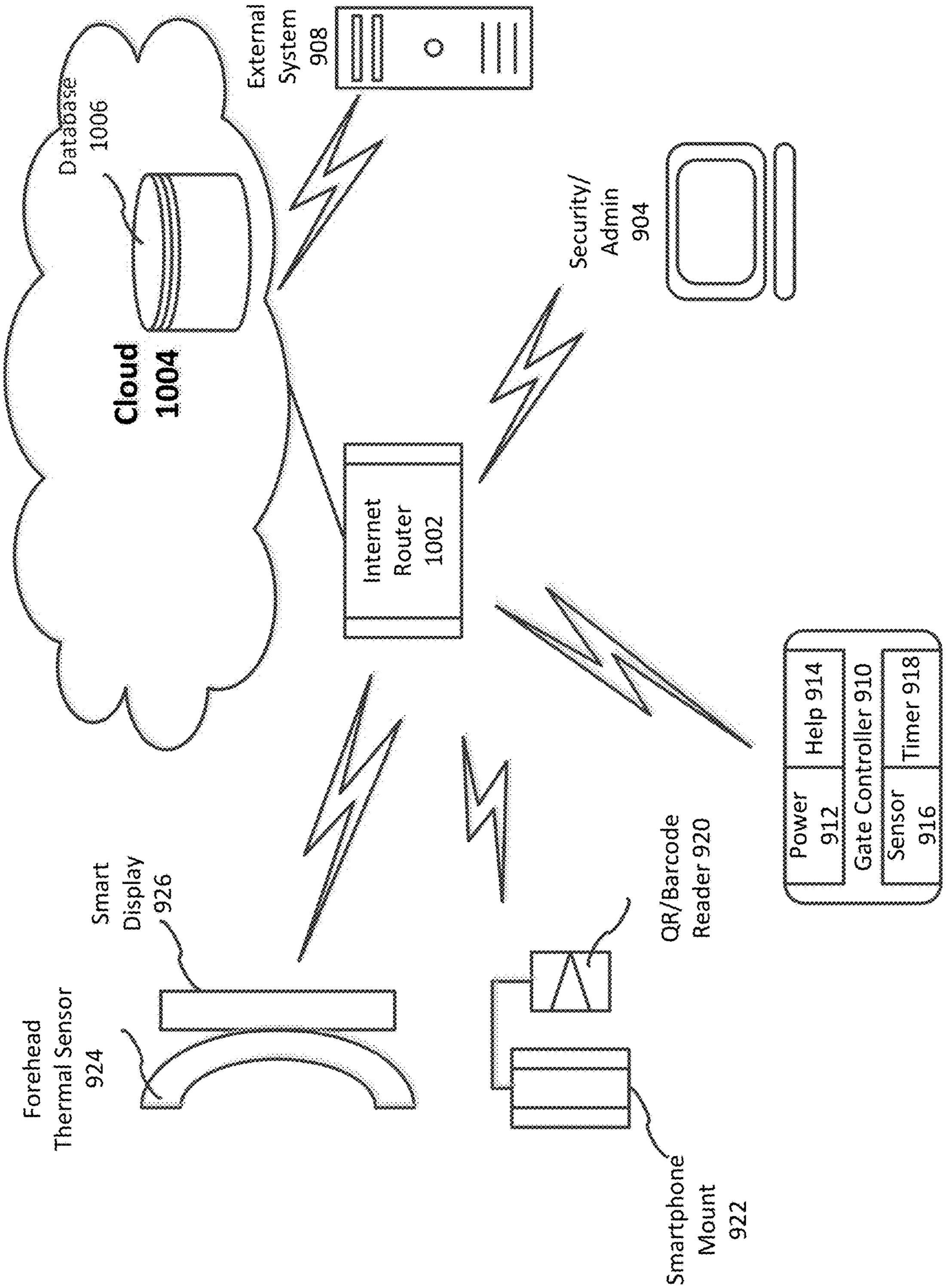
FIG. 10 is a schematic diagram of another exemplary smart gate system in accordance with exemplary aspects of the disclosure.

FIG. 10 is a schematic diagram of another exemplary smart gate system in accordance with exemplary aspects of the disclosure. Different from the arrangement in FIG. 9, the exemplary smart gate system utilizes cloud services 1004 for storage of health identification information of individuals, e.g., in a database service 1006, and for access control via gate operation. The smart gate system may be interconnected with an internet router 1002.

Figure 11:
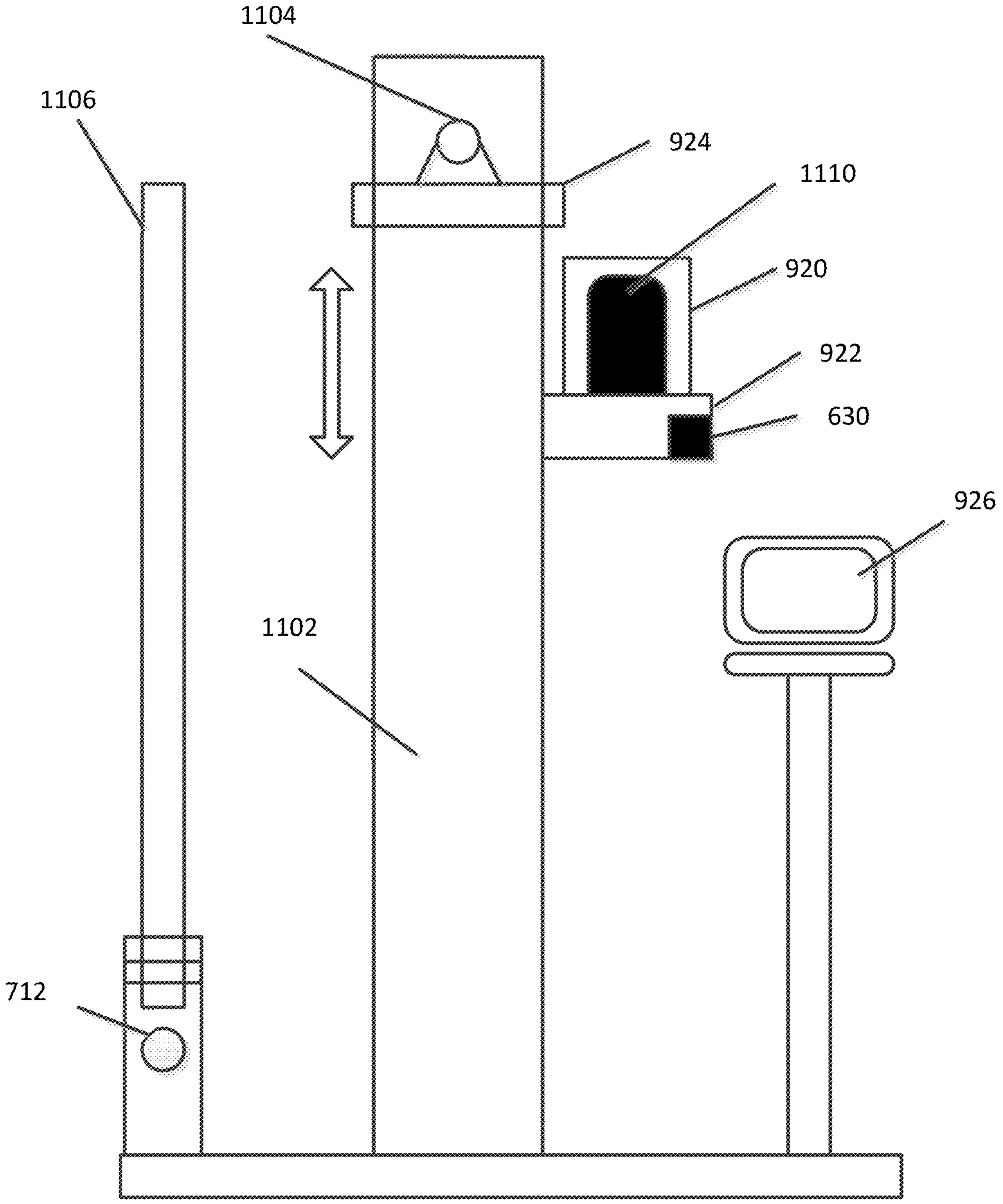
FIG. 11 illustrates an arrangement of a smart gate system in accordance with exemplary aspects of the disclosure.

FIG. 11 illustrates an arrangement of a smart gate system in accordance with exemplary aspects of the disclosure. An exemplary smart gate system 600 includes a QR code reader 920, as a connected tool, a thermometer 924, and a sensor 712. Data is transferred to a personal device 1110 including the Tawakkalna QR code and the QR code reader 920 retrieves the health status of the user based on the identification information that is encoded in the Tawakkalna QR code. The personal device 1110 is connected to an external database server 606. The connection to the external database server 606 is managed by the operating system of the personal device 1110, which may be a mobile phone or other portable display device. The thermometer 924 verifies that the temperature of a visitor does not rise and reach 38 degrees Celsius or more. The smart gate system 600 can include an emergency button 630. In the case of the occurrence of an emergency or other problem, a visitor can press the emergency button 630 to call and request a security person.

The arrangement may include a mount 922 for placing a smartphone and a motorized adjustable forehead thermometer 924 that moves vertically along a stand 1102. The Tawakkalna QR code is read by the QR code reader 920 when the smartphone 1110 is placed in the mount 922. The motorized adjustable forehead thermometer 924 automatically adjusts to the height of the person's forehead to read the body temperature. The automatic adjustment of the forehead thermometer 924 may be directed with the aid of a camera 1104 that captures the image of a visitor's face. A smart display 926 may display a pass or fail message to the user. In one embodiment, the smart display 926 may include a speaker that will output a sound to indicate a pass or fail. In one embodiment, the smart display 926 which when the thermal sensor is automatically position adjusted to the position of the user's forehead, a sound is output by the speaker of the smart display 926 when the user's forehead is in a position of the thermal sensor.

In one embodiment, once the Tawakkalna QR code is read and indicates the minimum required health identity, the camera 1104 will activate to capture an image of the visitor's face and cause the adjustable forehead thermometer 924 to move to the position of the visitor's forehead. In the case that the Tawakkalna QR code indicates an insufficient health identity, the smart display 926 will display a fail message, and the gate 1106 will remain in a closed position. In a case that the Tawakkalna QR code has indicated a sufficient health identity, and the temperature measured by the forehead thermometer 924 is within the required temperature range, the smart display 926 will display a pass message, and the gate 1106 will be moved to an open position.

In one embodiment, the Tawakkalna QR code is transmitted to a personal device 1110 each time a health event is recorded for the visitor. For example, a Tawakkalna QR code will be transmitted to the personal device 1110 when the visitor obtains a vaccination. A new Tawakkalna QR code may be transmitted when the visitor has another vaccination. If the visitor becomes infected and is diagnosed as such, another Tawakkalna QR code will be transmitted based on occurrence of that event.

In one embodiment, the Tawakkalna QR code is transmitted to a personal device 1110 when the visitor makes a request for the Tawakkalna QR code. The visitor may make a request for the Tawakkalna QR code when the visitor is in position to enter. The visitor may make a request for a QR code using the Tawakkalna App.

In one embodiment, the Tawakkalna QR code is transmitted to the personal device 1110 when the forehead thermometer 924 makes a measurement of the visitor's body temperature. If the measurement indicates that the visitor's body temperature exceeds a threshold temperature, thus indicating a fever, the QR code will not be transmitted, or instead of reading the QR code, a message, sound or visual alarm, or other communication will be made to indicate that the entry through the smart gate is denied.

In some embodiments, the Tawakkalna QR code will be given a date range, such that the QR code will expire after the end of the date range.

In some embodiments, the camera 1104 will capture an image of the visitor's face, and the smart gate system will use the captured image to authenticate the visitor. In such case, the Tawakkalna QR code will be transmitted to the personal device 1110 after the visitor is authenticated. The identification associated with the authenticated visitor will be paired with the QR code when the QR code reader reads the QR code.

The camera 1104 may be used to detect the presence of a face mask on the visitor's face, and the presence of the mask may be an additional factor used to allow or deny entry pass the gate.

Figure 12:
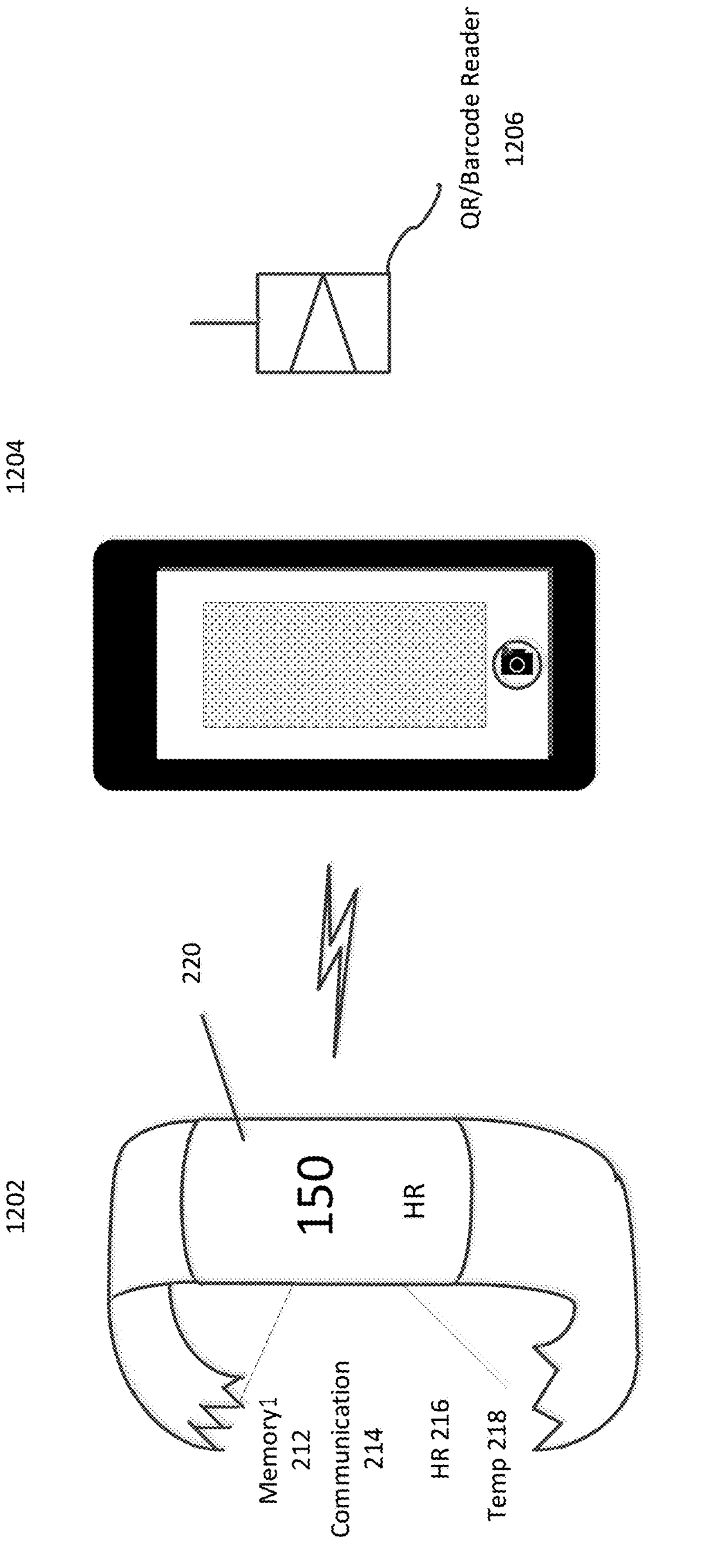
FIG. 12 is a diagram illustrating a smart gate system that utilizes a smart bracelet in accordance with exemplary aspects of the disclosure.

FIG. 12 is a diagram illustrating a smart gate system that utilizes a smart bracelet in accordance with exemplary aspects of the disclosure. In an embodiment, if a user is an employee, the user can connect to the smart gate system 600 through a smart bracelet 1202 (or a smartwatch) equipped with Near Field Communication (NFC) technology 214. The smart bracelet 1202 is configured to determine the health signs of the individual such as body temperature (thermometer 218), blood oxygen percentage, and heart rate 216, in addition to health status information stored in memory 212, including vaccination information and other health status information. The smart bracelet 1202 may include a display device 220. The smart gate system 600 checks for health identification through health status information transmitted from the smart bracelet 1202 (or the smartwatch) in conjunction with a mobile app 1204 that can display a Tawakkalna QR code that is read by a QR code reader 1206.

The smart gate system 600 records the employee or student's entry time and may provide the employee or student with a medical excuse in case the person's vital signs indicate a problem. Health status data can be saved using a portal. The portal provides a facility with a function to print many types of reports, such as general visitor reports, ate opening times, the time of employee entry, and other types of reports for an administrative or security person to review.

In one embodiment, smart bracelet 1202 may communicate directly with the gate controller 702, e.g., via NFC or Bluetooth, to signal the controller 702 to open the gate based on health status information previously stored in the smart bracelet 1202. In the embodiment, health status information may be earlier obtained by a scan of a Tawakkalna QR code that meets the required health standards, and prestored in a memory of the smart bracelet 1202. The health status information may have an associated expiration date range, in which the controller 702 will not open the gate when the date range of the health status information has expired.

In one embodiment, the gate is a door having a motor operated lock. The smart bracelet 1202 may communicate directly with the gate controller 702, e.g., via NFC or Bluetooth, to signal the controller 702 to unlock the door based on health status information previously stored in the smart bracelet 1202.

As an example of a smart bracelet, the Smart Bracelet "Nusk" of Saudi Arabia has been used for pilgrims for the hajj season during the pandemic. This smart bracelet 1202 contains information about the pilgrim's health, and if there was any possible exposure to COVID-19 and their health status, as well as the blood oxygen, heart rate, and emergency medical or any security assistance that it's equipped GPS technology can provide.

Users of the smart gate system may be divided into three categories: visitors, administrators, and security guards, each with different roles. A visitor is not always allowed to enter because they must meet the gate's conditions. An administrator's responsibilities include managing the conditions of the gate, appointing a security guard, ensuring the reports and database are accurate. In addition to providing support for the gate, the security guard must ensure that the smart gate system functions as intended and is open when a visitor completes these conditions. In addition, security guard may prepare reports and carry out the necessary checks to redress any problems encountered at the gate.

Figure 13:
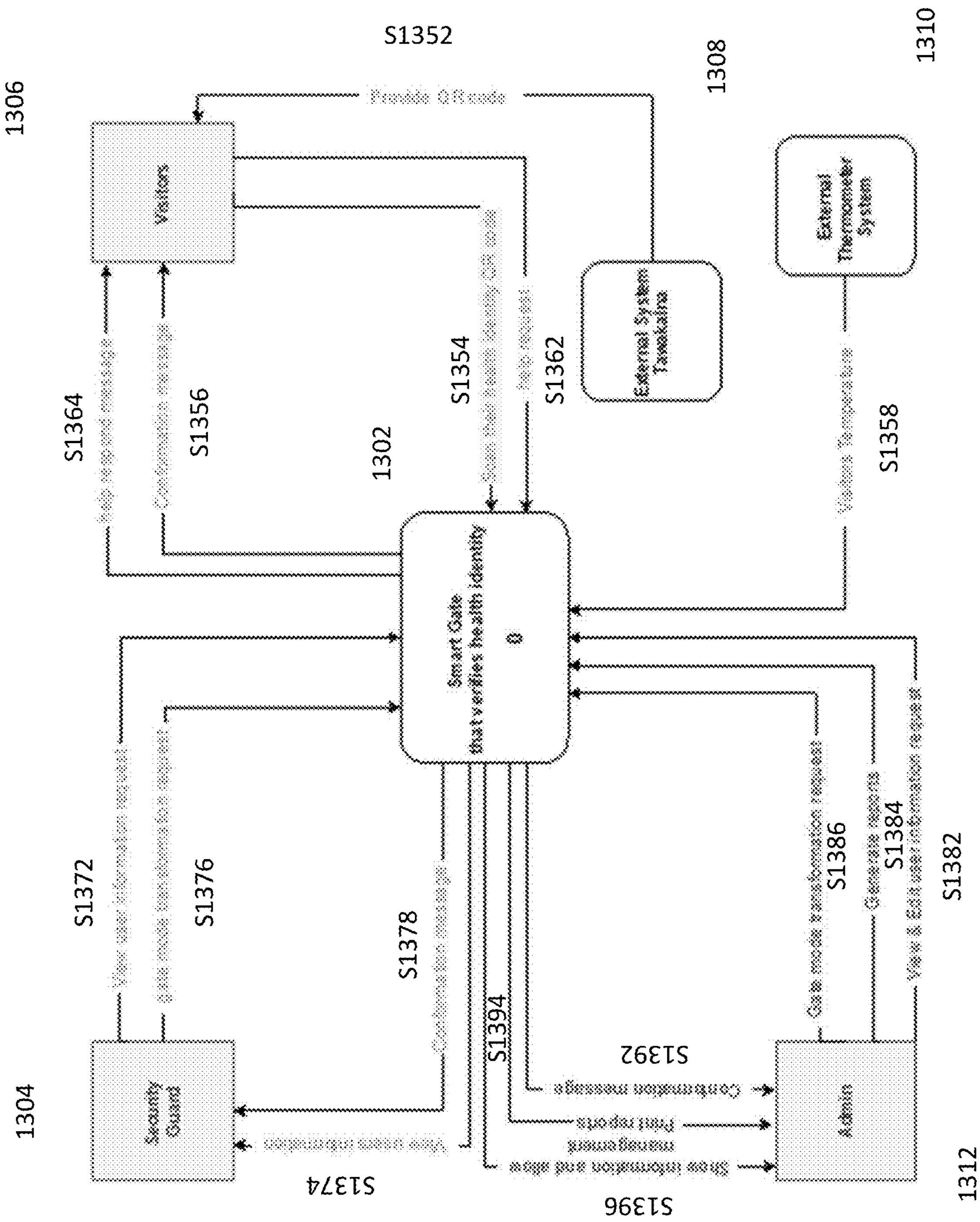
FIG. 13 is a data flow diagram for a smart gate system in accordance with exemplary aspects of the disclosure.

FIG. 13 is a data flow diagram (DFD) for the smart gate system. FIG. 13 illustrates an association between each user with the smart gate system. In FIG. 13 the DFD Context diagram contains the system entities (Admin 1312, Security guard 1304 and Visitors 1306) and their interaction with the smart gate system 1302 which is represented as a data flow between the entities and the system 1302. In S1352, a visitor 1306 will be provided with a QR code from the Tawakkalna system 1308. The QR code may be color coded as an indication of a visitor's movement status. Red means that the visitor cannot leave their premises. Yellow means that the visitor is quarantined for a certain period of time. Green means that the visitor is free to move. The color codes may indicate an immune class. In particular, a Dark Green Color code in Tawakkalna has three classes: (1) IMMUNE: the user has completed the doses of the Corona vaccine; (2) IMMUNE BY THE FIRST DOSE: the user has received a portion of the vaccines, and continues for 180 days; (3) IMMUNE BY RECOVERY: the user recovered from the infection and developed a natural immunity from the infection that lasts for six months. The Green Color indicates: No Record of Infection, and is declared healthy. Other colors may indicate that the user has been exposed to Covid 19 or has been infected by Covid 19.

In S1354, the QR code may be scanned by the smart gate system 1302. The QR code contains information of a personal health condition, as of a date and time, e.g., immune status of the person.

In addition, the visitor 1306 will have body temperature measured by a thermometer system 1310. In addition, in S1358, the visitor's body temperature will be transmitted to the smart gate system 1302.

In S1372, a security guard 1304 may request to view visitor health information. In S1374, the security guard 1304 may view the visitor's health information status. In S1356, the smart gate system 1302 will provide a message confirming or denying entry by the visitor. In S1376, the security guard 1304 may request a gate mode transformation request to the smart gate system 1302. In S1378, the smart gate system 1302 may send a confirmation message to the security guard 1304 to confirm the gate mode transformation request.

In an alternative use case, in S1362, the visitor 1306 may request help. In S1364, the smart gate system 1302 will provide a help response message to the visitor 1306.

An administrator 1312 may perform various actions with the smart gate system 1302, including, viewing and changing user information requests S1382, generating reports S1384, and authorizing a gate mode transformation request S1386. In response, the smart gate system 1302 may print reports S1394 and send messages S1392, S1396 to the administrator 1312. The administrator 1312 may be provided with information from the security guard 1304, including, in S1386, a request for gate mode transformation.

Figure 14:
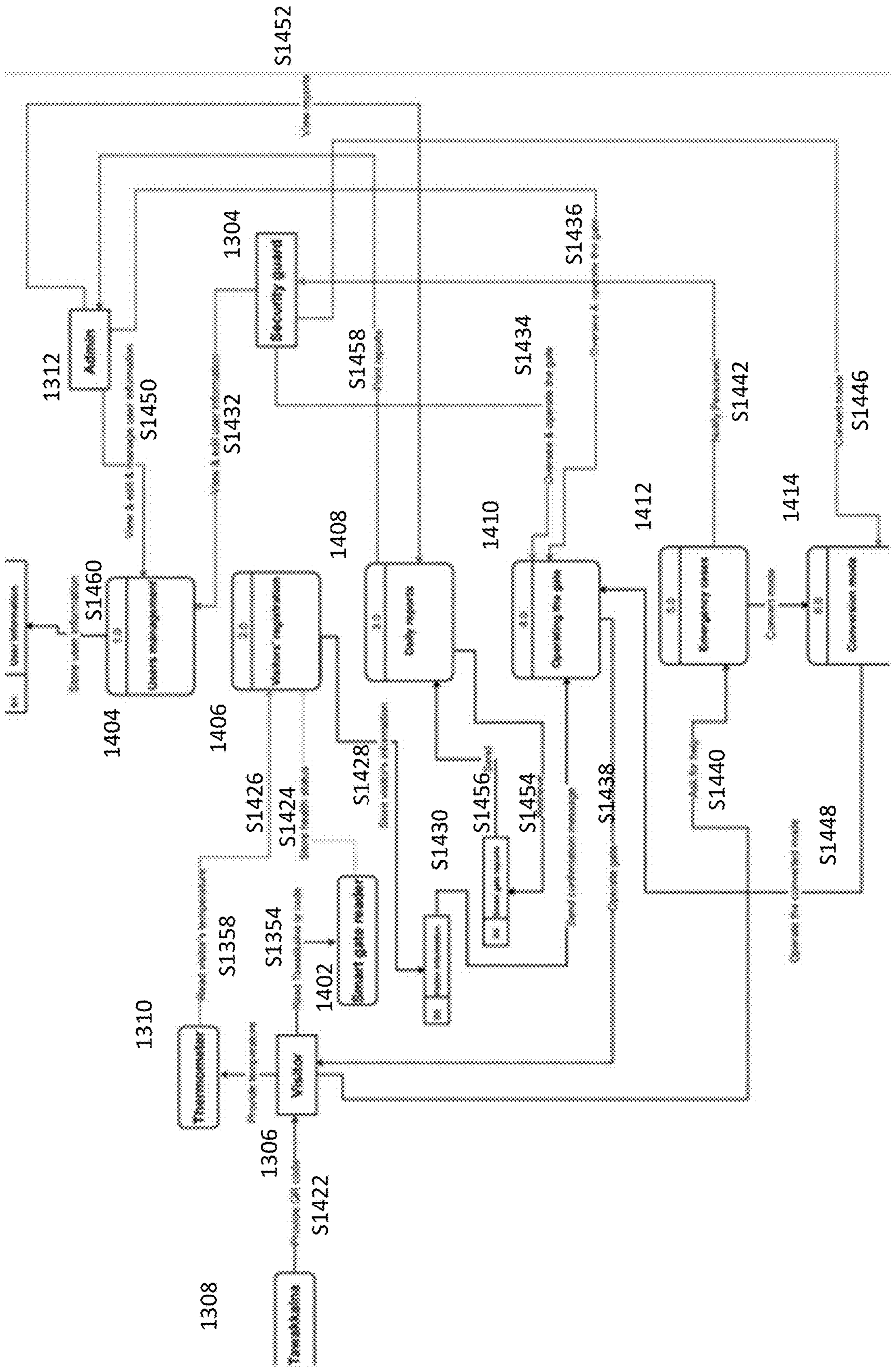
FIG. 14 is a detailed data flow diagram showing user interaction with the smart gate system in accordance with exemplary aspects of the disclosure.

FIG. 14 is a detailed data flow diagram showing user interaction with the smart gate system. In particular, FIG. 14 shows a more detailed DFD which illustrates how users interact with the system, how the system performs the process and where the data will be stored. In S1422, a visitor 1306 may obtain a QR code from the Tawakkalna system 1308. In S1358, a thermometer 1310 will measure the visitor's body temperature. In S1354, a smart gate QR reader 1402 will scan the Tawakkalna QR code from a personal device of the visitor 1306. In S1426, a visitor registration task 1406 will receive the visitor's body temperature from the thermometer 1310 and, in S1424, health status from the QR reader 1402. The visitor registration task 1406 will check the health status and temperature against entry criteria, and determine whether to grant or deny entry of the visitor 1306. In S1428, the visitor registration task 1406 will store the visitor's information in a database (606, 1006), and, in S1430, the database (606, 1006) will send a message to a gate operation task 1410, that confirms that the gate may be opened.

In S1432, the security guard 1304 may send a request to view, edit, manage visitor information managed by a user's management task 1404. The managed information of visitors is, in S1460, stored in the database 606, 1006. In S1434, the security guard 1304 may oversee and allow operation of the gate by the gate operation task 1410. In S1436, an administrator 1312 may also oversee and allow operation of the gate by the gate operation task 1410. In S1438, the gate operation task 1410 may send a message to the visitor 1306 that the gate will be opened and the visitor is allowed to go through the gate.

In one embodiment, in S1440, the visitor 1306 may send a request for help to an emergency task 1412. In S1442, the emergency task 1412 sends a notification message to the security guard 1304, and, in S1444, sends a convert mode command to a conversion mode task 1414. In S1446, the security guard 1304 may send a message to authorize a change in mode to the conversion mode task 1414. In S1448, the conversion mode task 1414 will then send a command to the gate operation task 1410 to operate the gate in the converted mode. In S1438, the gate operation task 1410 may send a message to the visitor 1306 that the gate will be opened and the visitor is allowed to go through the gate.

The administrator 1312 may request to view user information and view reports. In S1450, a user management task 1404 may receive a request to view, edit, manage user information and provide access to the user information stored in a database (606, 1006), as well as, in S1460, save user information in the database (606, 1006). In S1452, a reporting task 1408 may receive a request for a report, which, in S1454, will send a retrieve request to the database (606, 1006) and receive, in S1456, and generate the requested report. In S1458, the reporting task 1308 will send the report to the administrator 1312.

Figure 15:
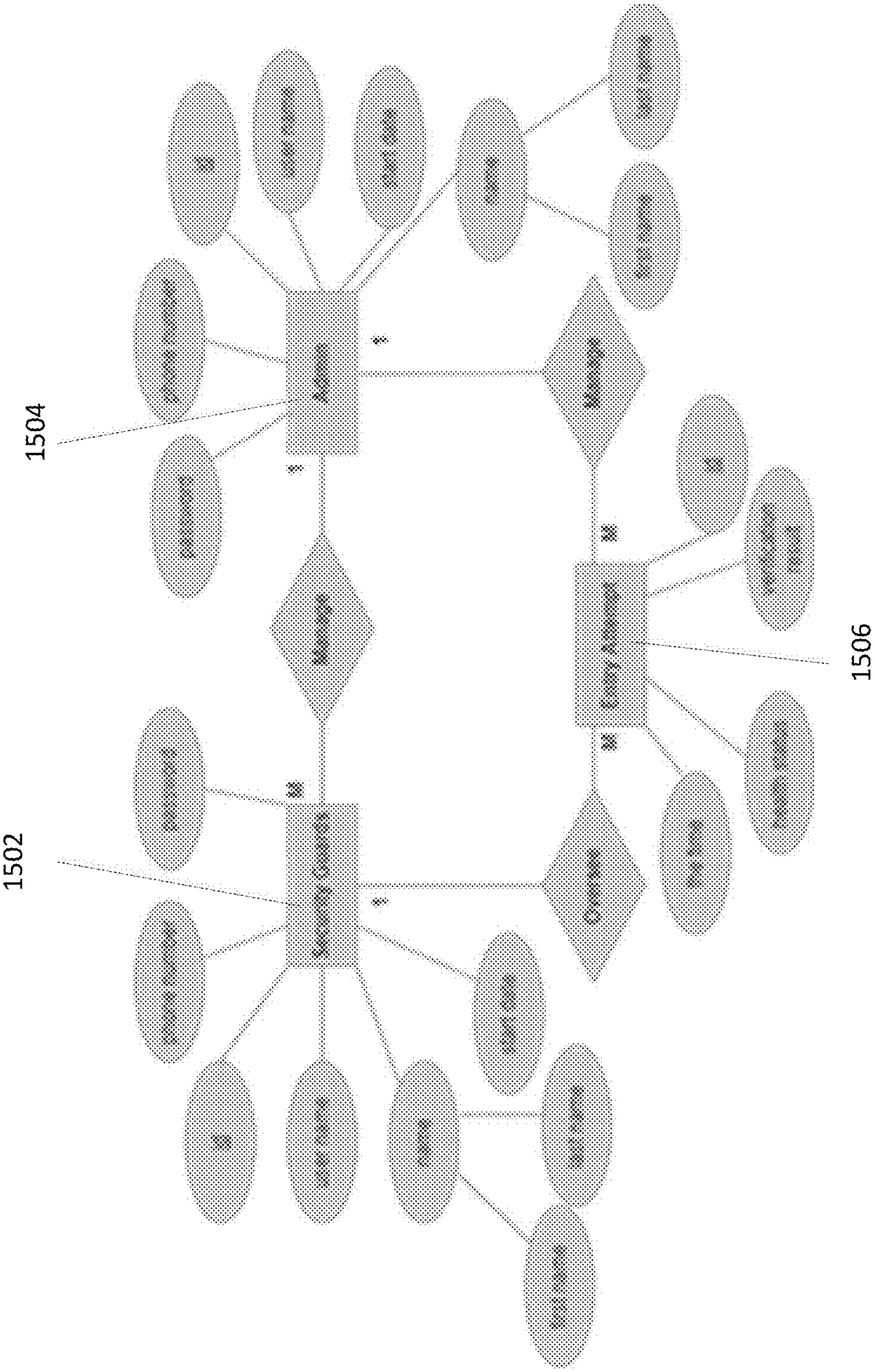
FIG. 15 is a diagram of relationships among data entities in accordance with exemplary aspects of the disclosure.

FIG. 15 is an entity relationship diagram for an example of data used in the smart gate system. The figure shows a relationship model for storing and managing all information retrieved by the system. Data is organized into entities within a database management system (606, 1006) accompanied by their attributes. There is data about significant entities along with their attributes. In FIG. 15, the entities are admin 1504, security guards 1502, and entry attempt entities 1506. The database management system (606, 1006) includes information about those entities and their attributes.

In an exemplary embodiment, attributes of the security guard 1502 can include name (first name, last name), start date, user name, password, a work ID, and a phone number. The attributes of the administrator 1504 can include name (first name, last name), start date, user name, password, a word ID and a phone number. The attributes of the entry attempt 1506 can include an ID, health status, verification result, and an entry time. Relationships can include one administrator 1504 manages M security guards 1502; a security guard oversees M entry attempts 1506; one administrator 1504 manages M entry attempts 1506.

Sequence diagrams are provided to show how and in what order a group of objects works together. In addition, the sequence diagrams model the logic of a sophisticated procedure, function, or operation as well as show how objects and components interact with each other to complete a particular process. The following sequence diagrams illustrate the possible scenarios in the Smart gate system.

Figure 16:
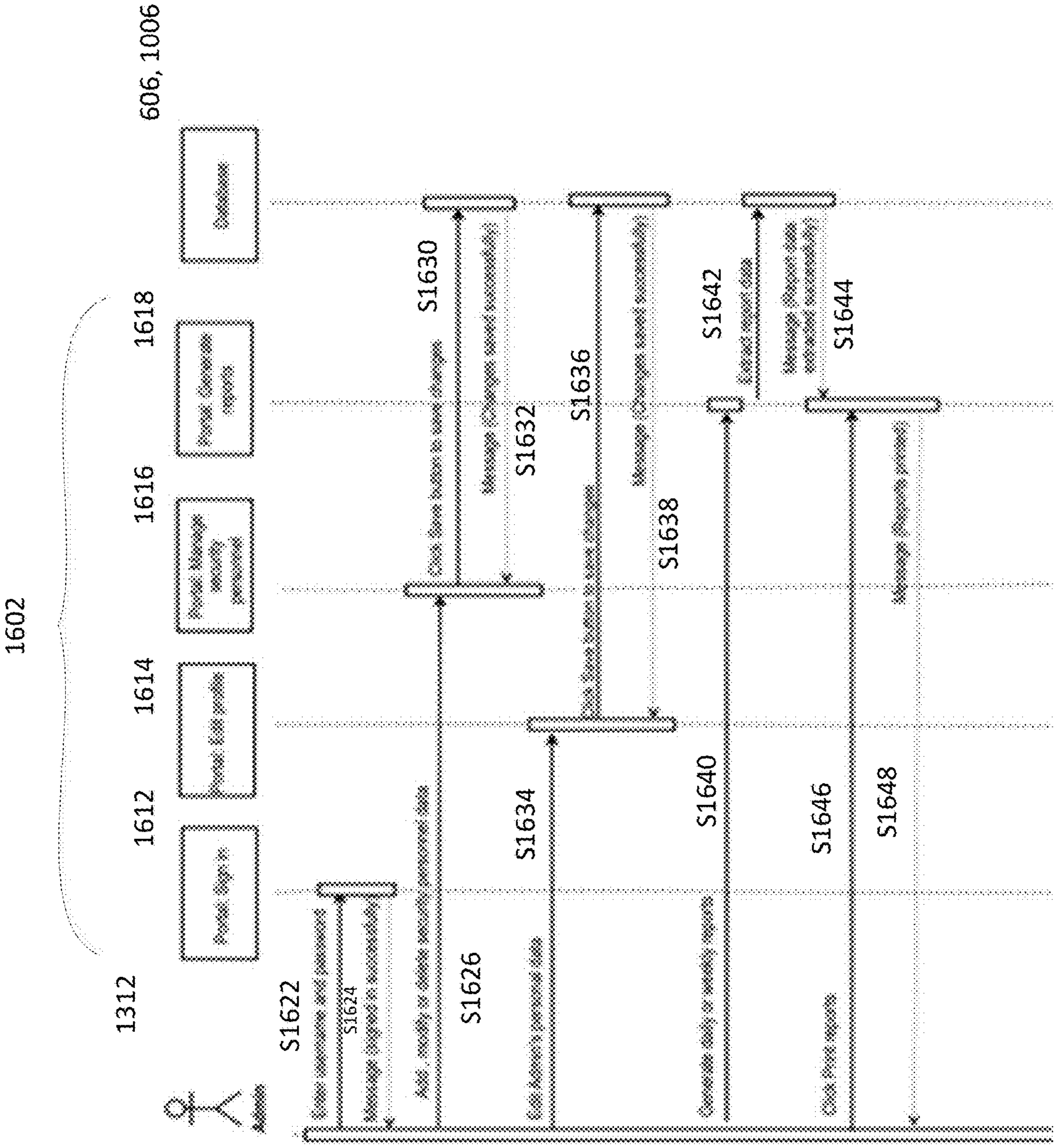
FIG. 16 is a sequence diagram for a smart gate that verifies health identity of an administrator in accordance with exemplary aspects of the disclosure.

FIG. 16 is a sequence diagram for a case of verifying health identity of an admin user (administrator 1312). The admin user 1312 can access the smart gate system 600 through a portal 1602. In an embodiment, the portal 1602 is a Web interface that is provided on a terminal computer. The terminal computer may be any of a desktop computer, laptop computer, tablet computer, to name a few. The portal 1602 can include a sign in function 1612, an edit profile function 1614, a manage security personnel function 1616, and a report request function 1618.

In the sign in function 1612, in S1622, an admin user 1312 can enter a username and password, and, in S1624, will receive a success message when the sign in is successful.

The admin user 1312 may have an associated user profile, which may be edited. The user profile may include a function to change a username and set a new password. The user profile may include personal data of the admin user 1312. The admin user 1312 may, in S1634, choose a function to edit the user profile in the edit profile function 1614, and, in S1636, save the changes in the database 606, 1006. In S1638, a message may be sent to the portal 1602 to verify that the changes to the user profile have been made.

In S1626, the admin user 1312 may use the manage security personnel function 1616 to add, modify, or delete security personnel data. In S1630, any changes made to the security personnel data may be saved in the database 606, 1006. In S1632, a message may be sent from the database 606, 1006, indicating that the changes have been saved successfully.

In S1640, the admin user 1312 may request periodic or ad hoc reports. The admin user 1312 may activate the report request function 1618. In S1642, the report request function 1618 submits a retrieval instruction to the database 606, 1006. When the data is retrieved, in S1644, the database 606, 1006 may send a message to the report request function 1618 indicating that the data has been obtained successfully. The report request function 1618 will generate the requested report and, in S1648, provide the generated report for viewing by the admin user 1312.

Figure 17:
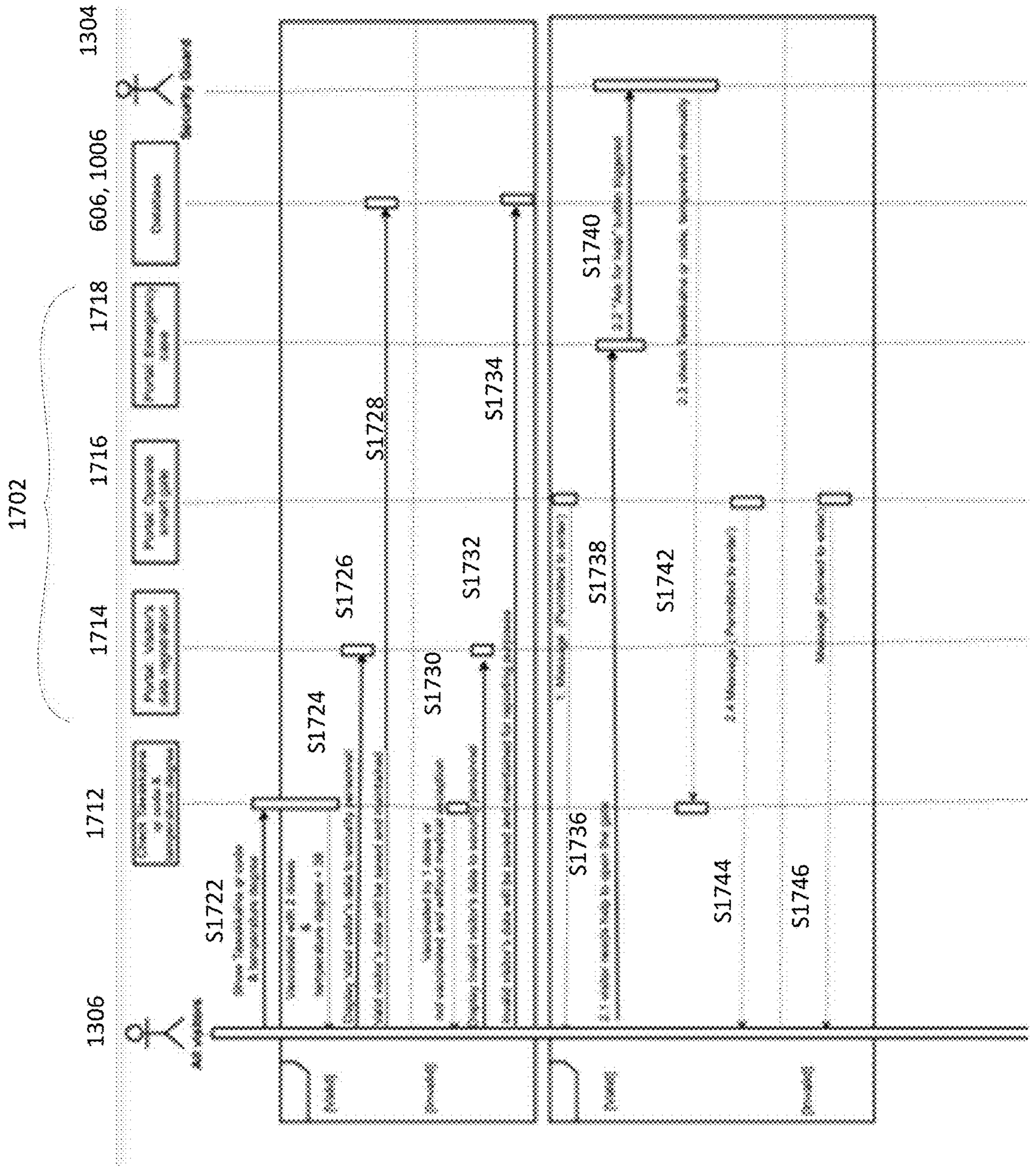
FIG. 17 is a sequence diagram for a smart gate that verifies health identity of all visitors in accordance with exemplary aspects of the disclosure.

FIG. 17 is a sequence diagram for a case of verifying health identity of a visitor with the aid of a security guard. A visitor 1306 can place a personal device into a mount, to quickly and easily have the Tawakkalna QR code read. In addition, a motor operated stand can adjust to the position of the visitor's forehead in order to accurately measure the visitor's body temperature. A QR code read and body temperature function 1712 reads, in S1722, and uses the QR code to determine whether the visitor's health information includes a vaccination for at least 2 doses and checks that the temperature degree is less than 38 degrees Celsius. A security guard 1304 can monitor the smart gate system 600 through a portal 1702. In an embodiment, the portal 1702 is a Web interface that is provided on a terminal computer. The portal 1702 can include a visitor's data registration function 1714, a smart gate operation function 1716, and an emergency condition function 1718.

With the visitor's data registration function 1714, in S1726, the security guard 1304 can view and verify the visitor's health status in portal 1702. In a case that the QR code read and body temperature function 1712 determines, in S1730, that the visitor's health information and the body temperature do not meet the required criteria, the visitor's data registration function 1714 will, in S1732, display in portal 1702 an indication that the visitor does not meet the required health criteria. In S1734, the data for an invalid visitor will be saved and maintained for reporting purposes in a database 606, 1006. The data for a valid visitor, including a data and time of verification, will be, in S1726, will be displayed in the portal 1714, and, in S1728, recorded and maintained in a database 606, 1006. In S1736, a message will be sent by the operate smart gate function 1716 to open the gate and permit the visitor to enter.

In S1738, a visitor 1306 may press a button, or provide a gesture, or voice command, to send an emergency request to open the gate, which will be handled by the emergency condition function 1718. In S1740, the emergency condition function 1718 will provide an indication to the portal 1702 that an emergency opening request is being made. In S1742, the security guard 1304 can manually check the temperature of the visitor or manually check both the temperature and QR code of the visitor. The security guard 1304 can send a command to the smart gate operation function 1716 to open the gate, or to deny entry of the visitor 1306. In S1744, the smart gate operation function 1716 will open the gate and send a message to the visitor 1306 that the visitor can proceed passed the gate. Otherwise, in S1746, the smart gate operation function 1716 will send a message to the visitor 1306 indicating that entry is denied, and a reason for the denial of entry.

Figure 18:
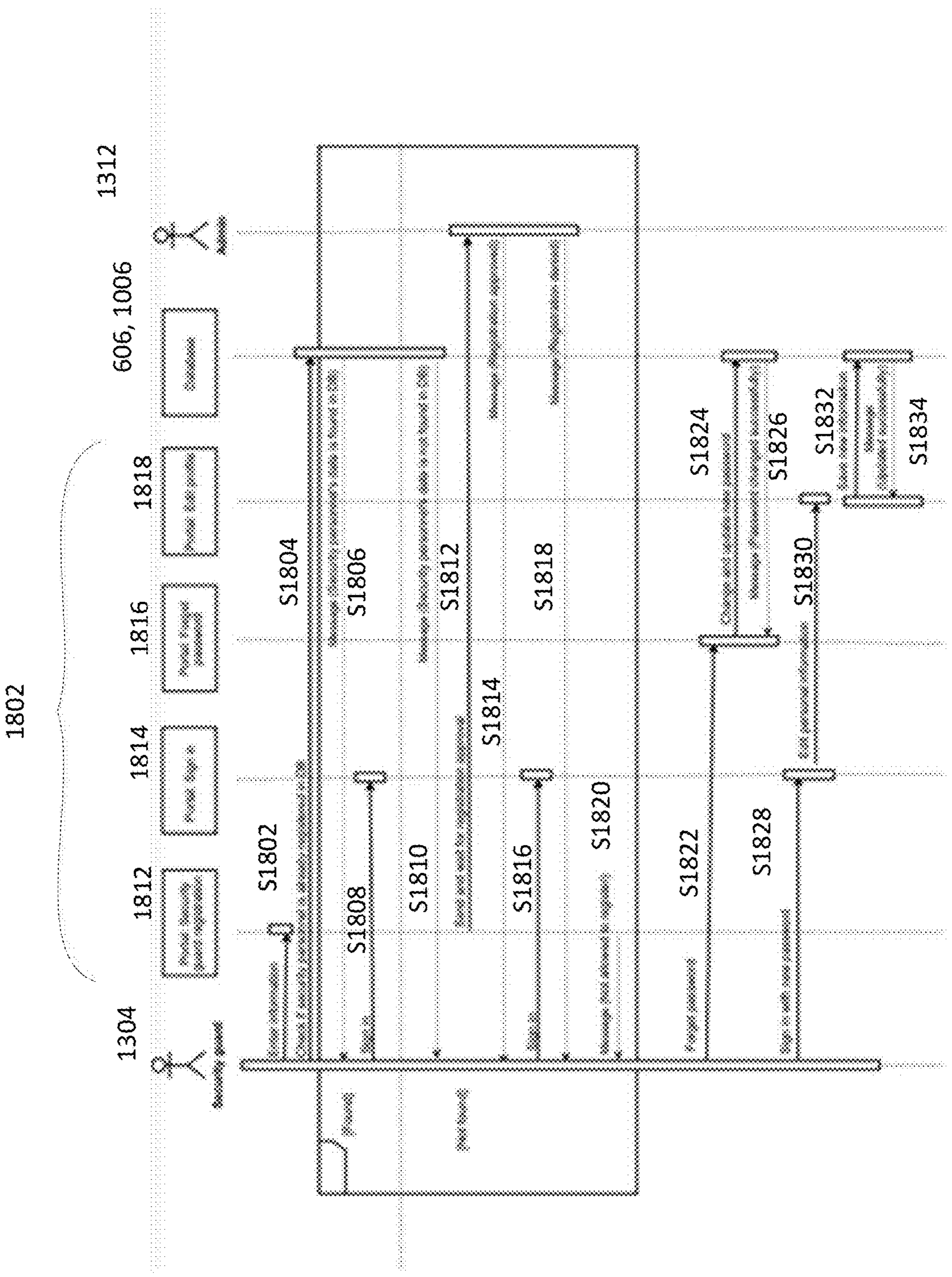
FIG. 18 is a sequence diagram for a smart gate that verifies health identity of a security guard in accordance with exemplary aspects of the disclosure.

FIG. 18 is a sequence diagram for a case of verifying health identify of a security guard. A security guard 1304 can access the smart gate system 600 through a portal 1802. In an embodiment, the portal 1802 is a Web interface that is provided on a terminal computer. The portal 1802 can include a security guard registration function 1812, a sign-in function 1814, a password function 1816, an edit profile function 1818.

In the security guard registration function 1812, in S1802, the security guard 1304 may begin by entering a registration request. In S1804, the smart gate system may check if the security person is already registered in the database 606, 1006. If the security person 1304 is already registered, in S1806, a message will be sent to the security guard portal. In S1808, the security guard 1304 may sign in. If the security guard is not registered, in S1810, the security person 1304 may receive a message indicating that security personnel data has not been stored in the database. In S1812, the security person may use the security guard registration function 1812 to send a request for registration to an admin user 1312. The admin user 1312 can decide whether to approve registration of the security person 1304. In S1814, if the security person 1304 receives a message that registration is approved, the security person 1304 may be provided with a form to submit registration information.

In the sign in function 1814, in S1816, the security person 1304 can enter and/or create a username and password, and will receive a success message when the sign in is successful.

In S1818, in the case that the security person 1304 receives a message that registration is denied by the admin user 1312, no further action can be made with regard to the smart gate system by the security person 1304. A password function 1816 may be used by the security guard 1304 to, in S1822, change a password. The database 606, 1006 may, in S1824, store the changed password, and, in S1826, send a message indicating that the password change is successful. In S1828, the sign in function 1814 may be used to sign in with the new password.

An edit profile function 1818 may, in S1830, be used by the security guard 1304 to edit the profile of the security guard. In S1832, the edit profile function 1818 may save the profile information in the database 606, 1006, and, in S1834, send a message indicating that changes have been successfully made to the profile and stored in the database 606, 1006.

Figure 19:
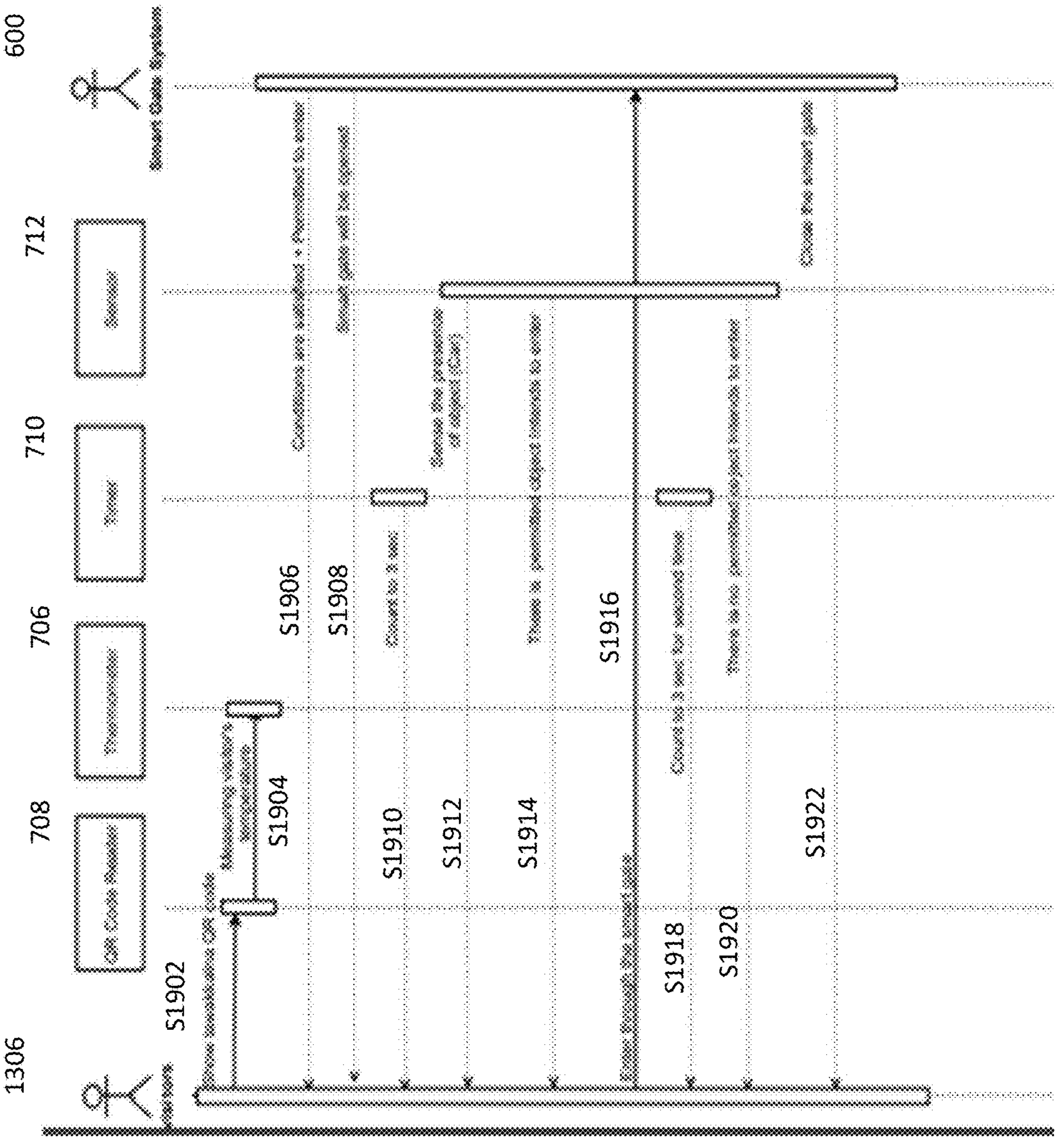
FIG. 19 is a sequence diagram for a case of verifying health identity in accordance with exemplary aspects of the disclosure.

FIG. 19 is a sequence diagram for a case of verifying health identity. The smart gate system 600 includes a QR code reader 708, as a connected tool, a thermometer 706, a timer 710, and a sensor 712. Data is transferred to a personal device 608 in the form of a QR code and, in S1902, the QR code reader 708 extracts the health status of the user that is encoded in the QR code. The personal device 608 is connected to an external database server 606. The connection to the external database server 606 is managed by the operating system of the personal device 608, which may be a mobile phone or other portable display device. In S1904, the thermometer 706 measures the visitor's body temperature and, in S1906, the smart gate system 600 verifies the health conditions of the visitor are satisfied and that the temperature of a visitor 1306 does not reach 38 degrees Celsius or more. The smart gate system 600 can include an emergency button 630. In the case of the occurrence of an emergency or other problem, a visitor 1306 can press the emergency button 630 to call or request a security person.

The smart gate system 600 includes a gate operation mechanism 622. The gate operation mechanism 622 includes a motor unit for opening and closing a gate 620, a controller for controlling the motor, a motion sensor 712, such as an infrared sensor or laser, for determining whether a visitor 1306 is passing the gate 620 boundary, and a timer mechanism 710. In S1908, in the case that the health conditions of the visitor are satisfied and the temperature is with acceptable range, the smart gate will open the gate. In S1910, the gate operating mechanism 622 may close the gate 620 based on the timer mechanism 710. In an example embodiment, the closing process depends on timing by the timer mechanism 710 that, in S1918, times out in 3 seconds, followed by, in S1914, a sensor 712 that checks the passage of the visitor 1306 pass the opened gate 620. In S1920, if the visitor 1306 does not pass the opened gate within the 3 seconds, the timer restarts. In S1922, the gate 620 is closed three seconds after the visitor 1306 has passed the gate 620. A purpose of the timing mechanism 712 is to control flow of visitors through the smart gate in order to optimize the flow, as well as to prevent another visitor(s) from passing through the smart gate without being verified. The time out setting of the timing mechanism 710 may be adjustable and may be set at a different time out period.

Figure 20:
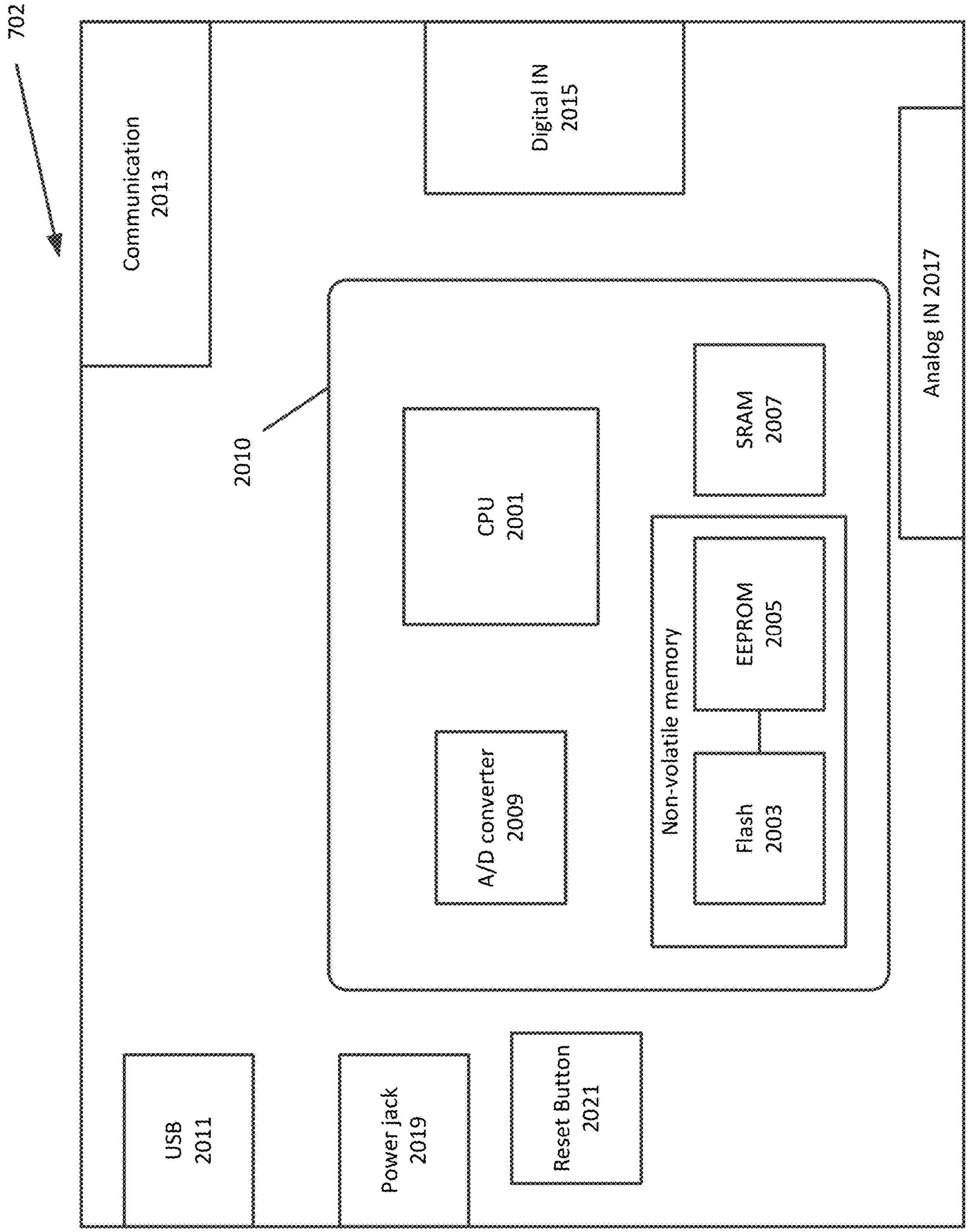
FIG. 20 is a block diagram of general components of a microcontroller.

FIG. 20 is a block diagram of general components of a microcontroller. The computer-based control system 702 may be implemented as a microcontroller. A microcontroller 2010 may contain one or more processor cores (CPUs 2001) along with memory (volatile and non-volatile) and programmable input/output peripherals. Program memory in the form of flash 2003, ROM, EPROM, or EEPROM 2005 is often included on chip, as well as a secondary RAM 2007 for data storage. In one embodiment, the computer-based system 702 is an Arduino integrated circuit board 702 with a microcontroller 2010. The board includes digital I/O pins 2015, analog inputs 2017, hardware serial ports 2013, a USB connection 2011, a power jack 2019, and a reset button 2021. Although the Arduino is a widely used microcontroller-based board, it should be understood that other microcontroller configurations are possible. Variations can include the number of pins, whether or not the board includes communication ports or a reset button.

The microcontroller 2010 is a RISC-based microcontroller having flash memory 2003, SRAM 2007, EEPROM 2005, general purpose I/O lines, general purpose registers, a real time counter, flexible timer/counters, an A/D converter 2009, and a JTAG interface for on-chip debugging. The microcontroller 2010 is a single SOC. Although the description is of a particular microcontroller product, it should be understood that other microcontrollers may be used. Microcontrollers vary based on the number of processing cores, size of non-volatile memory, the size of data memory, as well as whether or not it includes an A/D converter or D/A converter.

Numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosure. For example, this technology may be structured for cloud computing whereby a single function is shared and processed in collaboration among a plurality of apparatuses via a network.

The invention claimed is:

1. A smart gate system with temperature responsive control, comprising:

a thermal sensor for measuring a temperature of a visitor and transmitting the measured temperature;

a QR code reader to read a health status QR code and transmitting a message including health status information of the visitor in accordance with the health status QR code and a request for entry, the health status QR code having a predetermined date range;

a database system for receiving and maintaining the health status information and registered visitor information;

a gate controller receiving a control signal for permitting or denying entry through a gate, wherein the gate controller includes a power source, a help button, an object detection sensor and a timer;

a server for determining that the health status information and the temperature of the visitor obtained from the thermal sensor indicate that the visitor has not contracted a predetermined virus and that the visitor is a registered visitor, and responding to the request for entry by transmitting the control signal to the gate controller in accordance with the determination and whether the health status QR code is within the predetermined date range; and a screen protector;

wherein the gate controller controlling opening of the gate based on the control signal that permits entry through the gate;

wherein the thermal sensor is a forehead thermal sensor for measuring body temperature at a user's forehead, when the thermal sensor is automatically position adjusted to the position of the user's forehead, a sound is output by a sound output device when the user's forehead is in a position of the thermal sensor, wherein the screen protector includes a cover means to cover the forehead temperature sensor with a protective sheath material, wherein the protective sheath material is provided on a supply spool in the form of long rolled individual sheets and is advanced onto a take up spool after each use of the forehead temperature sensor, wherein the supply spool is equipped with a resistive despool decelerator such as a friction wheel to hinder excessive release of the sheath, wherein the protective sheath material is configured with a conductive path traveling longitudinally through a length of conductive polymer, a capacitive sensor mounted on one or both of the supply spool or the take up spool makes electrical contact with the conductive path to measure and record a capacitance value, the capacitance value reflects contact between and individual and the protective sheath material during a measurement occurrence on the forehead thermal sensor, and wherein the microcontroller includes program instructions to advance the take up spool after a cycle of capacitative measurements.

2. The smart gate system of claim 1, further comprising:

a personal display device which is used to securely obtain the health status QR code, wherein the QR code reader reads the health status QR code from a display of the personal display device when the thermal sensor reads the temperature of the visitor.

3. The smart gate system of claim 2, wherein the server is a cloud service, the thermal sensor, QR code reader, personal display device, and gate controller wirelessly communicate with the cloud service via the Internet.

4. The smart gate system of claim 2, wherein the server does not transmit a health status QR code to the personal display device when the temperature reading from the thermal sensor is above a normal range.

5. The smart gate system of claim 2, further comprising:

a mount for holding the personal display device in a position for reading by the QR code reader.

6. The smart gate system of claim 1, wherein upon reading the health status QR code, the QR code reader compares a date of the reading against the predetermined date range, wherein when the date of the reading is after the predetermined date range, the QR code reader transmits a message indicating that the health status QR code has expired, and wherein the gate controller receives a control signal denying entry through the gate based on the expiration of the QR code.

7. The smart gate system of claim 1, further comprising:

an emergency override in which a command can be sent to the gate controller and used to allow entry through the gate without a temperature measurement from the thermal sensor.

8. The smart gate system of claim 1, wherein the QR code reader records a current date when the health status QR code is read, and wherein the gate controller denies entry through the gate when the predetermined date range of the health status QR code is after the current date, indicating that the health status QR code has expired.

9. A smart gate system with temperature responsive control, comprising:

a thermal sensor for measuring a temperature of a visitor and transmitting the measured temperature;

a QR code reader to read a health status QR code and transmitting a message including health status information of the visitor in accordance with the health status QR code and a request for entry, the health status QR code having a predetermined date range;

a database system for receiving and maintaining the health status information and registered visitor information;

a screen protector;

a gate controller receiving a control signal for permitting or denying entry through a gate, wherein the gate controller includes a power source, a help button, an object detection sensor and a timer;

a server for determining that the health status information and the temperature of the visitor obtained from the thermal sensor indicate that the visitor has not contracted a predetermined virus and that the visitor is a registered visitor, and responding to the request for entry by transmitting the control signal to the gate controller in accordance with the determination and whether the health status QR code is within the predetermined date range; and the gate controller controlling opening of the gate based on the control signal that permits entry through the gate;

wherein the thermal sensor is a forehead thermal sensor for measuring body temperature at a user's forehead, when the thermal sensor is automatically position adjusted to the position of the user's forehead, a sound is output by a sound output device when the user's forehead is in a position of the thermal sensor, wherein the screen protector includes a cover means to cover the forehead temperature sensor with a protective sheath material, wherein the protective sheath material is provided on a supply spool in the form of long rolled individual sheets and is advanced onto a take up spool after each use of the forehead temperature sensor, wherein the supply spool is equipped with a resistive despool decelerator such as a friction wheel to hinder excessive release of the sheath, wherein the protective sheath material is configured with a conductive path traveling longitudinally through a length of conductive polymer, a capacitive sensor mounted on one or both of the supply spool or the take up spool makes electrical contact with the conductive path to measure and record a capacitance value, the capacitance value reflects contact between and individual and the protective sheath material during a measurement occurrence on the forehead thermal sensor, and wherein the microcontroller includes program instructions to advance the take up spool after a cycle of capacitative measurements;

a motorized adjustable stand having a temperature sensor for obtaining temperature of the user's forehead, wherein the motorized adjustable stand automatically position adjusts the temperature sensor to the position of the user's forehead.

* * * * *